United States Patent [19]
Bray, Jr.

[11] Patent Number: 4,893,630
[45] Date of Patent: Jan. 16, 1990

[54] APPARATUS AND METHOD FOR ANALYZING PHYSIOLOGICAL CONDITIONS WITHIN AN ORGAN OF A LIVING BODY

[75] Inventor: Robert S. Bray, Jr., Houston, Tex.

[73] Assignee: Trinity Computing Systems, Inc., Houston, Tex.

[21] Appl. No.: 597,518

[22] Filed: Apr. 6, 1984

[51] Int. Cl.[4] ............................................. A61B 5/00
[52] U.S. Cl. .................................... 128/671; 128/748
[58] Field of Search .............................. 128/670–671, 128/748, 731–732

[56] References Cited

U.S. PATENT DOCUMENTS

| | | | |
|---|---|---|---|
| Re. 29,008 | 10/1976 | Ott .................................... | 128/774 X |
| 3,696,808 | 10/1972 | Roy et al. ............................ | 128/731 |
| 3,725,690 | 4/1973 | Hjorth ................................ | 128/731 X |
| 3,943,915 | 3/1976 | Severson ............................ | 12/748 X |
| 4,062,354 | 12/1977 | Taylor et al. ..................... | 128/748 X |
| 4,080,653 | 3/1978 | Barnes, Jr. et al. ............. | 128/748 X |
| 4,092,981 | 6/1978 | Ertl .................................... | 128/731 |
| 4,201,224 | 5/1980 | John .................................. | 128/731 |
| 4,214,591 | 7/1980 | Sato et al. ......................... | 128/731 |
| 4,217,912 | 8/1980 | Hubmann et al. ................ | 128/774 |
| 4,236,125 | 10/1980 | Schneider ........................ | 128/731 X |
| 4,254,779 | 3/1981 | Miyata et al. ...................... | 128/731 |
| 4,265,252 | 5/1981 | Chubbuck et al. ............... | 128/748 |
| 4,279,258 | 7/1981 | John .................................. | 128/731 |
| 4,305,400 | 12/1981 | Logan ................................ | 128/670 |
| 4,602,644 | 7/1986 | DiBenedetto et al. .......... | 128/671 X |

OTHER PUBLICATIONS

"EEG Analysis Based on Time Domain Properties", Bo Hjorth, Electroencephalography and Clinical Neurophysiology, Elsevier Publishing Co., Amsterdam, Netherlands, 1970.

Daley et al, "Fluctuation of Intracranial Press. Assoc with the Cardiac Cycle", Neurosurgery, vol. 11, No. 5, 11–1982, pp. 617–621.

Wilkinson et al; "Nunvolumetric Methods of Detecting Imparied Intracranial Compliance or Reactivity"; J. Neurosurg, vol. 50, 6–1979, pp. 758–767.

Oster; Muscle Sounds, pp. 108–114.

Avezaat et al; "Cerebrospinal Fluid Pulse Press and Intracranial vol.-Press Relationships", J. Neurol., Neursurg, and Psych., 1979, 42, pp. 687–700.

Portnoy et al.; "Cerebrospinal Fluid Pulse Wave as an Indicator of Cerebral Nutoreg."; J. Neurosurg., vol. 56, 5–1982-pp. 666–678.

Shapiro et al; "Characteriz. of Clin. CSF Dynamics and Neural Axis Compliance Using the P-V Index"; Annals of Neurol., vol. 7, No. 6, 6–1980, pp. 508–514.

Shapiro et al; "Clin. Applic. of the P.V Index in Treatment of Pediatric Head Injuries"; J. Neurosurg., vol. 56, 6–1982, pp. 819–825.

Primary Examiner—Angela D. Sykes
Attorney, Agent, or Firm—Vaden, Eickenroht, Thompson & Boulware

[57] ABSTRACT

An apparatus and method for analyzing physiological conditions in an organ of a living body is disclosed. The pressure within the organ is measured over a period of time and converted to digital electrical signals via a pressure transducer and a digital to analog converter. The digital electrical signals are mathematically analyzed with Fourier transforms and centroid analysis to obtain information concerning changes in physiological conditions in the organ.

23 Claims, 6 Drawing Sheets

APPARATUS AND METHOD FOR ANALYZING PHYSIOLOGICAL CONDITIONS WITHIN AN ORGAN OF A LIVING BODY

This invention relates to an apparatus and method for analyzing physiological conditions within an organ of a living body and, more particularly, to the analysis of changes in waveforms generated by pressure variations within an organ of the body.

BACKGROUND OF THE INVENTION

The apparatus and method of the invention will be described with reference to the problem of acquiring information concerning the physiological status of the brain by measuring and analyzing variations of pressure within the brain. The invention may also be used to acquire information concerning the physiological status of other types of body organs.

Each time the heart beats, it forces blood out into the arteries of the body. A portion of this blood enters the skull to supply oxygen and nutrients to the brain. The pumping of the blood by the heart creates a pulsation of the blood through the arteries. This pulsation of the blood in the arteries of the brain contributes to the fluid pressure levels in the brain. The fluid pressure in the brain is generally referred to as the "intracranial pressure" or "ICP". The intracranial pressure is dependent upon several factors including the elastic characteristics of the brain, the volume of cerebro-spinal fluid in the brain and the rate of flow of the blood in the brain.

The flow of blood to the brain is automatically regulated by the body to avoid increases in intracranial pressure that might damage the brain. In addition, other regulatory processes in the body operate to keep the level of the intracranial pressure within safe limits. Some of these other regulatory processes include the formation and absorption of cerebro-spinal fluid, maintenance of carbon dioxide levels in the blood, etc. When the brain is subjected to head trauma, internal bleeding, brain tumors or other abnormal conditions, the intracranial pressure may rise to dangerous levels. If the body's regulatory processes are not able to control the increased intracranial pressure, then death may result.

In the treatment of such abnormal brain conditions it is desirable to know the magnitude of the mean value of the intracranial pressure. If the mean intracranial pressure is increasing with time, a worsening of the patient's condition is indicated and remedial steps may be taken. Techniques currently in use for monitoring changes in intracranial pressure involve the placement of a pressure monitoring device into the skull of the patent to directly measure the actual pressure inside the patient's head. As the blood pulses through the brain, an intracranial pressure waveform is produced. The mean value of the intracranial pressure waveform is taken to be the mean value of the intracranial pressure.

The mean value of the intracranial pressure, however, defines only one parameter in a complex systems of forces operating within the brain. As mentioned above, increases in the intracranial pressure may also be compensated for by changes in carbon dioxide levels in the blood, rate of blood flow, cerebro-spinal fluid formation and absorption and other factors. Because of the interrelationship between these factors, the mean value of the intracranial pressure often shows changes only after the compensating mechanisms have failed. For this reason there have been many attempts made to develop techniques for measuring and monitoring both the cerebral blood flow and the elastic properties of the brain.

The elastic capacity of the brain is referred to as the "cerebral compliance". Compliance is defined as the change in pressure per unit volume of added fluid. One technique currently in use for the measurement of the compliance of the brain involves the injection of fluid into the patient's intracranial cavity and the direct measurement of the resulting changes in the intracranial pressure. This technique can provide valuable information concerning the degree of severity of a brain injury. However, the technique has severe limitations due to the fact that injections of fluid into the brain may produce dangerous increases in intracranial pressure. Risks of infection are also present. In addition, the injection of fluid may only be done a very few times (often only once every day or two) with the risk of infection and other complications increasing with every injection. For these reasons this technique has not been widely practiced. There currently exists no known prior art system for acquiring information concerning cerebral compliance on a continuous on-line real time basis.

In addition, no known prior art technique exists for measuring the changes in the regulation of cerebral blood flow on a continuous on-line real time basis. Complex techniques exist for performing a one time measurement of cerebral blood flow using either injectable tracers or absorbable gases. These techniques, however, are not useful for the continuous monitoring of cerebral blood flow changes.

SUMMARY OF THE INVENTION

The apparatus and method of the invention provides means for measuring changes in cerebral compliance and changes in cerebral blood flow in a patient on a continuous on-line real time basis and means for simultaneously recording the intracranial pressure.

The basic principle upon which the apparatus and method of the invention operates is that the brain resonates at a given frequency each time the heart beats. This resonance is due to arterial blood being forced under pressure through the blood vessels of the brain in a pulsatile fashion. The characteristics of this resonance are affected by at least two major parameters. These parameters are (1) the stiffness of the brain which is related to the cerebral compliance and (2) the characteristics of the flow of blood through the brain, i.e., the cerebral blood flow.

The apparatus and method of the invention continuously measure and records the intracranial pressure waveform (the "ICP waveform"), analyzes the frequency distribution of the ICP waveform to obtain information from the ICP waveform concerning changes in the brain stiffness parameter and changes in the blood flow parameter. The measured values of these two parameters may be correlated to known values of cerebral compliance and cerebral blood flow from single point determinations from noncontinuous off-line techniques to yield the actual quantified values of cerebral compliance and cerebral blood flow for the patient being monitored. In addition, the information obtained may be useful in determining volumetric changes in the cerebro-spinal fluid.

More particularly, the invention provides means for converting the analog ICP waveform into digital signals and then analyzing the digital signals using fast Fourier transforms and centroid analysis to obtain the vibrational characteristics of the brain. For example, as the brain becomes stiffer it resonates or vibrates at a higher frequency within a characteristic range of frequencies. As the brain becomes softer, it resonates at a lower frequency. Measurement of this change in frequency yields an estimate of cerebral compliance. Similarly, cerebral blood flow has a representative component within the ICP waveform. As the body regulates cerebral blood flow within the brain, the shape of the ICP waveform changes in a definite manner. The changes in the ICP waveform correspond to measurable frequency changes that provide an estimate of the cerebral blood flow in the brain.

The invention permits the acquisition and on-line real time computer analysis of information concerning cerebral compliance and cerebral blood flow and the simultaneous correlation of that information with the patient's intracranial pressure. Changes in the patient's condition may be detected at a very early stage well before any change may be detected in the patient's mean intracranial pressure. Often by the time the patient's mean ICP reading begins to change, it is too late to take any remedial action and the patient may suffer neurologic damage or die. With the "early warning" provided by the monitoring system of the invention, the attending physician may detect the beginning of a change in the patient's condition before the intracranial pressure rises to dangerous levels. The additional information provided by the monitoring system of the invention concerning cerebral compliance and cerebral blood flow may be used by the attending physician in evaluating and determining the appropriate therapeutic response in a given case.

An object of the invention is to provide an apparatus and method for analyzing physiological conditions within an organ of a living body.

Another object of the invention is to provide an apparatus and method for analyzing changes in the waveforms generated by variations of the intracranial pressure in the brain of a patient on a continuous on-line real time basis.

Another object of the invention is to provide an apparatus and method for measuring changes in the cerebral compliance of the brain of a patient and for measuring changes in the cerebral blood flow of the brain of a patient on a continuous on-line real time basis.

Still another object of the invention is to provide means for measuring and recording the intracranial pressure waveform, analyzing the frequency distribution of the intracranial pressure waveform to obtain information concerning the changes of cerebral compliance and cerebral blood flow in the brain of a patient.

Yet another object of the invention is to provide means for converting an analog intracranial pressure waveform into digital signals and analyzing the digital signals using fast Fourier transforms and centroid analysis to obtain information concerning the intracranial pressure, the cerebral compliance and the cerebral blood flow of the brain.

Other objects and advantages of the invention will become apparent from a consideration of the detailed description and the drawings.

DESCRIPTION OF THE PREFERRED EMBODIMENT

Figure 1:
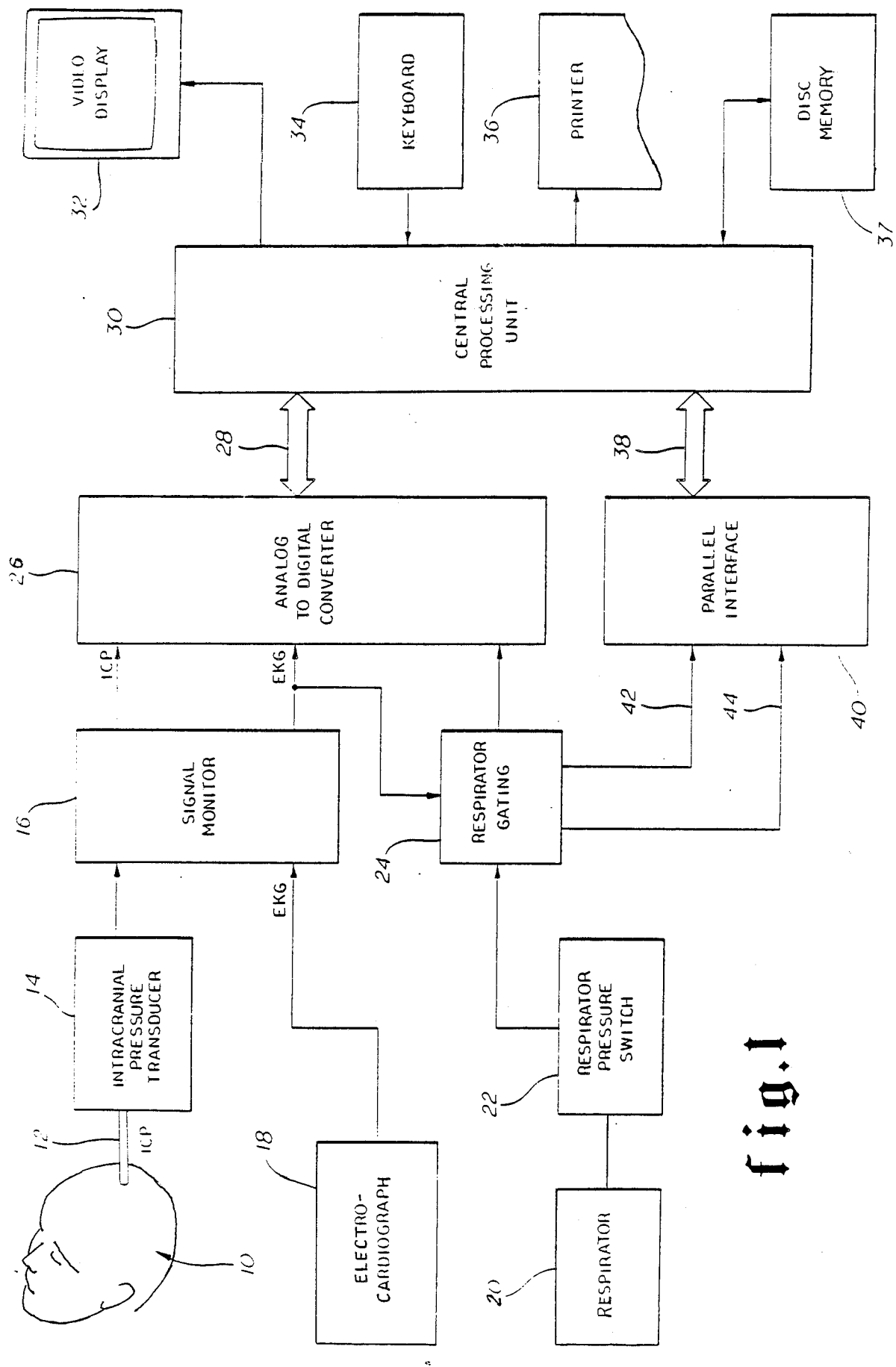
FIG. 1 is a schematic block diagram showing the interconnection of the components of the apparatus.

As shown schematically in FIG. 1, the patient 10 must undergo an operation in which a small plastic sensor tube 12 is placed into the ventricle of the patient's brain. The sensor tube 12, referred to as a ventriculostomy, is formed having a small axial passageway through it. The intracranial fluid of the patient's brain fills the axial passageway of sensor tube 12 and transmits the intracranial pressure within the patient's brain to an intracranial pressure transducer 14 at the end of sensor tube 12. The intracranial pressure transducer 14 generates an analog voltage signal that is proportional to the intracranial pressure within the brain that is being detected by sensor tube 12. The analog voltage signal representing the intracranial pressure varies over time thereby forming the intracranial pressure waveform. Other forms of intracranial pressure sensors may also provide information suitable for analysis. Alternatively, extracranially positioned pressure sensors may also be used to detect signals that contain information concerning the changes in intracranial pressure.

The intracranial pressure ("ICP") waveform signal is transmitted to a signal monitor 16 for visually monitoring the ICP waveform of the patient. A number of different types of signal monitors 16 may be used for the purpose of monitoring the ICP waveform signal. However, because many commercially available signal monitors do not record signals having very high frequencies, it may be necessary to electronically modify the circuitry of a signal monitor 16 so that it may detect and record signals having frequencies in the range of zero (0.0) cycles per second to thirty five (35.0) cycles per second. Such modifications is within the skill of a person having ordinary skill in the art.

A standard electrocardiograph 18 connected to the patient generates an analog voltage signal that provides information concerning the patient's heartbeat. This electrocardiograph ("EKG") signal varies over time thereby forming the EKG waveform. The EKG waveform is transmitted to the signal monitor 16 as shown in FIG. 1. The EKG waveform possesses information that permits the determination of the time relationship between the patient's heartbeat and the resulting cerebral blood flow.

A standard respirator 20 is connected to the patient and a respirator pressure switch 22 is placed into the exhalation valve (not shown) of the respirator 20 in order to obtain information concerning the respiratory cycle of the patient. The respirator pressure switch 22 is a low volume alarm switch capable of determining the timing of each exhalation of the patient's breath. As will be explained more fully below, the respirator pressure switch 22 actuates the respirator gating means 24 to gate the EKG signal.

The ICP and EKG analog waveform signals are transmitted to an analog to digital converter 26 (generally referred to as the "ADC unit"). The ADC unit 26 converts the analog waveform signals of the ICP and EKG into digital signals representing the respective values of the ICP and the EKG analog signals. The digital signals of the ICP and EKG are transmitted from the ADC unit 26 via data bus 28 to the central processing unit 30 (generally referred to as the "CPU"). The CPU 30 is connected to standard computer peripherals including a video display 32 such as a cathode ray tube, a keyboard 34 for input of operator control signals, a printer 36 for recording the information stored and processed in the CPU 30 and a disc memory 37 for on-line storage of data. The CPU 30 is also connected via data bus 38 to a parallel interface unit 40. As will be described more fully below, parallel interface unit 40 receives information via signal lines 42 and 44 concerning the status of certain switches in the respirator gating means 24. The CPU 30 can electronically monitor the status of the switches via the parallel interface unit 40 and data bus 38.

The following types of equipment were used to reduce the invention to practice. The types of equipment listed below are illustrative only and other equivalent types of equipment may be used. A Hewlett Packard quartz pressure transducer was used for pressure transducer 14 and a Cordis ventriculostomy tube was used for sensor tube 12. A Hewlett Packard Patient Monitoring System was used for signal monitor 16. Electrocardiograph 18 was incorporated within and a part of the Hewlett Packard Patient Monitoring System. Respirator 20 was a standard volume ventilator. A Tecmar PC-Mate Lab Master board contained the analog to digital converter and associated timing circuitry. The central processing unit was an IBM PC-XT with 512 K of memory and with an 8087 math co-processor for increasing the speed with which the mathematical computations were performed. The video display 32, keyboard 34, printer 36 and disc memory 37 were all standard IBM compatible computer peripherals.

It has been empirically determined by the inventor that the brain exhibits different values of cerebral compliance and cerebral blood flow depending upon whether the patient is inhaling or exhaling. This is due to the fact that the normal process of breathing causes changes in thoracic pressure which affects the venous flow of blood from the brain. Therefore, in order to obtain a more regular and correct correlation of the EKG signal with the ICP waveform it is desirable to record the EKG signal only during one half of the respiratory cycle. This information may also be therapeutically useful for determining the acceptable limits of ventilation for a particular patient.

Figure 2:
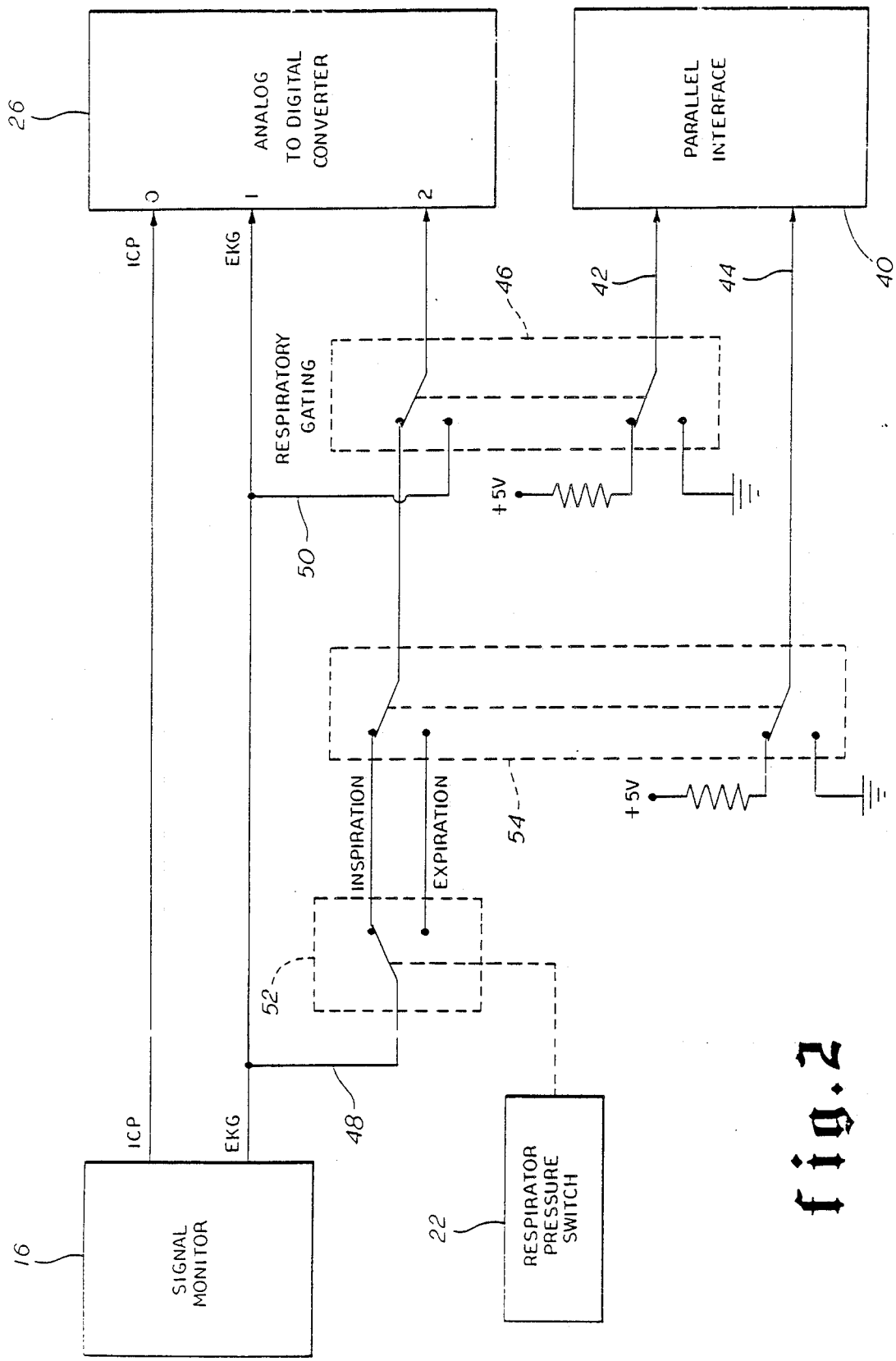
FIG. 2 is a schematic circuit diagram showing the operation of the respirator gating means.

The specially constructed respirator gating means 24 is shown in detail in FIG. 2. Respirator gating means 24 permits the EKG signal to be gated to an additional input port in the ADC unit 26 either only during the inspiration half of the respiratory cycle or only during the expiration half of the respiratory cycle. As shown in FIG. 2, the EKG signal is continually transmitted to the ADC unit 26 at the input port labelled "1". The gated EKG signal is transmitted to the ADC unit 26 at the input port labelled "2" during the selected half of the respiratory cycle.

As shown in FIG. 2, a manually operated dual switch 46 controls whether the respiratory gating of the EKG signal will be enabled. When switch 46 is in the "up" position as shown, then the EKG signal present on signal line 48 can reach the number "2" input port of the ADC unit 26 when the other switches are also appropriately set. When switch 46 is in the "up" position, then signal line 42 is connected to a voltage source which provides a signal to CPU 30 via the parallel interface unit 40 and data bus 38 that indicates that the respiratory gating mode has been selected. When switch 46 is in the "down" position, then the EKG signal reaching the number "2" input port of the ADC unit 26 is the ungated EKG signal present on signal line 50. When switch 46 is in the "down" position, then signal line 42 is connected to ground and no signal is present on signal line 42. CPU 30 interprets the absence of a signal on signal line 42 as an indication that the respiratory gating mode has not been selected.

Automatically operated switch 52 is operated in response to the output of respirator pressure switch 22. When the patient is breathing in, then respirator pressure switch 22 causes switch 52 to move to the "up" position within signal line 48 as shown in FIG. 2. When the patient is breathing out, then respirator pressure switch 22 causes switch 52 to move to the "down" position within signal line 48.

A manually operated dual switch 54 determines whether the inspiration half or the expiration half of the respiratory cycle will be selected. When switch 54 is in the "up" position as shown, then the EKG signal present on signal line 48 can reach the number "2" input port of the ADC unit 26 only when the patient is breathing in (and switch 46 is in the "up" position to enable respiratory gating). When switch 52 is in the "up" position, then signal line 44 is connected to a voltage source which provides a signal to CPU 30 via the parallel interface unit 40 and data bus 38 that indicates that the inspiration half of the respiratory cycle has been selected. When switch 54 is in the "down" position, then the EKG signal present on signal line 48 can reach the number "2" input port of the ADC unit 26 only when the patient is breathing out (and switch 46 is in the "up" position to enable respiratory gating). When switch 52 is in the "down" position, then signal line 44 is connected to ground and no signal is present on signal line 44. CPU 30 interprets the absence of a signal on signal line 44 as an indication that the expiration half of the respiratory cycle has been selected.

The ICP analog waveform signal and the gated EKG analog waveform signal are transmitted to the ADC unit 26 where the analog waveform signals are converted into digital values. The digital values are transmitted via data bus 28 to the CPU 30 where they serve as input to the computer program for mathematically analyzing the waveform signals.

Figure 3:
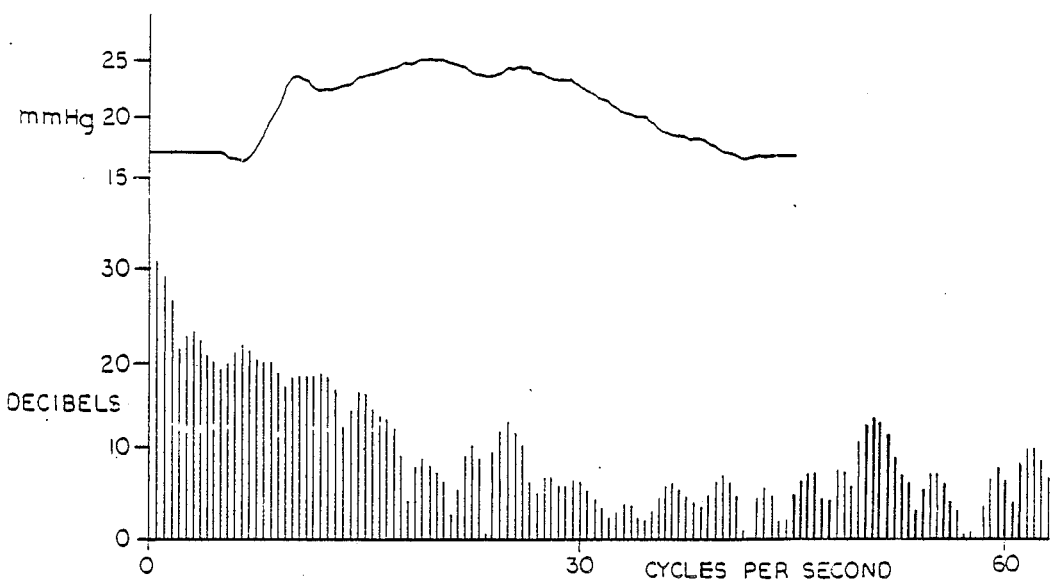
FIG. 3 is a schematic representation of a typical intracranial pressure waveform and its corresponding frequency distribution.

The computer program employs a fast Fourier transform algorithm of a type well known in the art to calculate the frequency distribution of the ICP waveform. The Fourier transform yields the spectrum of the ICP waveform in the form of the power density as a function of frequency. A typical ICP waveform and its corresponding frequency distribution are shown in FIG. 3. The majority of the frequency contribution is seen to be due to the lower frequencies. Because the decibel vertical co-ordinate for the frequency distribution is on a logarithmic scale, it is seen that the higher frequencies have a much smaller contribution than the lower frequencies.

In addition to the fast Fourier transform algorithm, the computer program comprises a number of specially written subroutines for preparing the input data, calculating the centroid of a range of frequencies, rejecting data due to artifacts in the data acquisition process, trending and plotting the data, and similar functions. The detailed mathematical calculations involved in the algorithms and subroutines are set forth in the listing of the computer program in the Appendix.

The frequency distribution of the ICP waveform comprises the range of frequencies created by the vibration of the brain. It has been empirically determined that the brain resonates or "rings" at a frequency of approximately eight (8.0) cycles per second. Of course, this "resonant" frequency of the brain is merely the predominant frequency of a range of frequencies present in the frequency distribution of the measured ICP waveform. The measured ICP waveform may have components of frequency with frequencies up to twenty-five (25.0) cycles per second. Beyond this limit there is little contribution to the ICP waveform due to the fact that the brain does not resonate at high frequencies.

It has been empirically observed that the cerebral compliance of the brain is correlated with the value of the centroid of a range of frequencies around approximately eight (8.0) cycles per second. The centroid is a center of balance of the range or "window" of frequencies that represents the point where the frequency distribution is mainly concentrated. The cerebral compliance centroid (Centroid 2 in the computer program) is calculated from a window of frequencies chosen with the lower limit of four (4.0) cycles per second and with the upper limit of fifteen (15.0) cycles per second. Of course, other ranges of frequency would be chosen for other types of organs depending upon the resonance characteristics of the particular organ being monitored. As the cerebral compliance increases, so does the value of the cerebral compliance centroid. In physical terms this means that as the brain becomes "stiffer" it resonates or "rings" at a higher frequency. As the cerebral compliance decreases, so does the value of the cerebral compliance centroid. In physical terms this means that as the brain becomes "softer" it resonates or "rings" at a lower frequency. By monitoring the value of the cerebral compliance centroid over time it is possible to obtain information concerning the status of the patient's cerebral compliance on a continuous on-line real time basis.

Similarly, it has been empirically determined that the cerebral blood flow of the brain is correlated with the value of the centroid of a range of frequencies around approximately one and one half (1.5) cycles per second. The cerebral blood flow centroid (Centroid 1 in the computer program) is calculated from a window of frequencies chosen with the lower limit of two tenths (0.2) cycles per second and with the upper limit of three (3.0) cycles per second. As the cerebral blood flow increases, so does the value of the cerebral blood flow centroid. In physical terms this means that as the blood flows more quickly through the brain, the brain resonates or "rings" at a higher frequency. As the cerebral blood flow decreases, so does the value of the cerebral blood flow centroid. In physical terms this means that as the blood flows more slowly through the brain, the brain resonates or "rings" at a lower frequency. By monitoring the value of the cerebral blood flow centroid over time it is possible to obtain information concerning the status of the patient's cerebral blood flow on a continuous on-line real time basis.

At very low levels of cerebral blood flow anomalous condition has been empirically observed. When the rate of cerebral blood flow drops to twenty five (25.0) to twenty (20.0) milliliters of blood per one hundred (100.0) grams of brain per minute, then the value of the cerebral blood flow centroid goes up instead of down as one would normally expect. At such low levels of cerebral blood flow, the value of the cerebral compliance centroid goes down as one would normally expect. These results are due to the fact that at such low levels of cerebral blood flow there is no longer enough blood flow to generate the resonant frequency in the brain.

The listing of the computer program set forth in the Appendix discloses in detail the techniques used to mathematically analyze the ICP waveform signals. The computer program comprises one master program called "ICP" and a number of subroutines. The master program calls the subroutines to perform specific tasks. One subroutine initializes the analog to digital converter 26 to receive the analog ICP and EKG waveform signals. The trigger subroutine initiates data acquisition in response to the timing signals derived from the EKG waveform signal. The acquisition subroutine acquires the desired channels of information and stores them in an array within the memory of the central processing unit 30. The windowing subroutine selects exactly one complete cycle of data. The fast Fourier transform subroutine calculates the frequency distribution of the ICP waveform. The centroid subroutine calculates the cerebral compliance centroid and the cerebral blood flow centroid. The plotting subroutine graphically presents the data of the ICP waveform and the calculated values of the centroids. Similarly, the printing subroutine prints out the relevant data.

In summary form, the actual calculations occur in the following order. The central processing unit 30 waits for the QRS complex component of the EKG waveform which signals the beginning of a cardiac cycle. The central processing unit 30 then collects data at one hundred (100) samples per second per channel for two hundred fifty six (256) points of data. Then, the data is windowed to obtain exactly one full cycle with the ending pressure equal to the beginning pressure. The remainder of the array in which the data is placed is filled with zeros. Next the Fourier transform is calculated and the results of that calculation are used to calculate the centroids. As previously explained, the cerebral compliance centroid is presently calculated from a window of frequencies from four (4.0) cycles per second to fifteen (15.0) cycles per second and the cerebral blood flow centroid is calculated from a window of frequencies from two tenths (0.2) cycle per second to three (3.0) cycles per second. These values are under operator control and may be changed through the computer program. The values of the two centroids may then be printed or plotted on the video display 32 or the printer 36. In addition, either the original ICP and EKG waveforms or the transform of the ICP waveform may be graphically displayed on video display 32. The data may also be stored in the disc memory 37 for later retrieval and off-line analysis.

Figure 4:
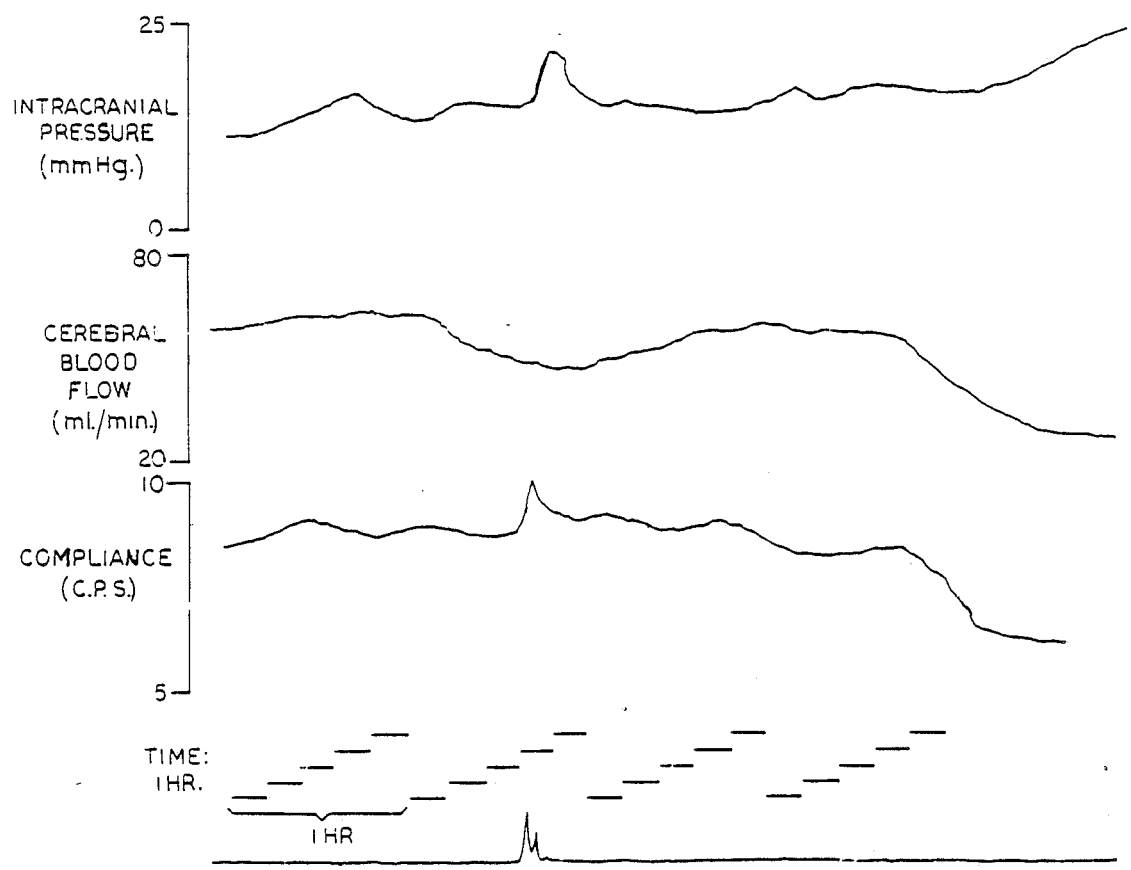
FIG. 4 is a schematic representation of how information concerning the mean intracranial pressure, the cerebral blood flow and the cerebral compliance may be graphically displayed.

FIG. 4 depicts an example of how the data and the results of the analysis may be graphically displayed on video display 32 or on printer 36. The time scale on the graph shows five time segments of twelve minutes each for each hour of time. The time segments are staggered vertically for ease of recognition. The mean intracranial pressure is plotted in units of millimeters of mercury ("mmHg") versus time. The cerebral blood flow is plotted in units of milliliters per minute ("ml/min") versus time. The cerebral compliance is plotted in units of cycles per second ("cps") versus time. A graph of signal abberations due to artifacts in the recording process is displayed with the data to aid in the detection of erroneous readings.

The on-line real time simultaneous trending of the cerebral blood flow information and the cerebral compliance information together with the simultaneous presentation of the mean intracranial pressure in the form described above provides a valuable diagnostic tool for use in a variety of clinical situations. The value of the diagnostic technique may be seen by considering a few examples.

Figure 5:
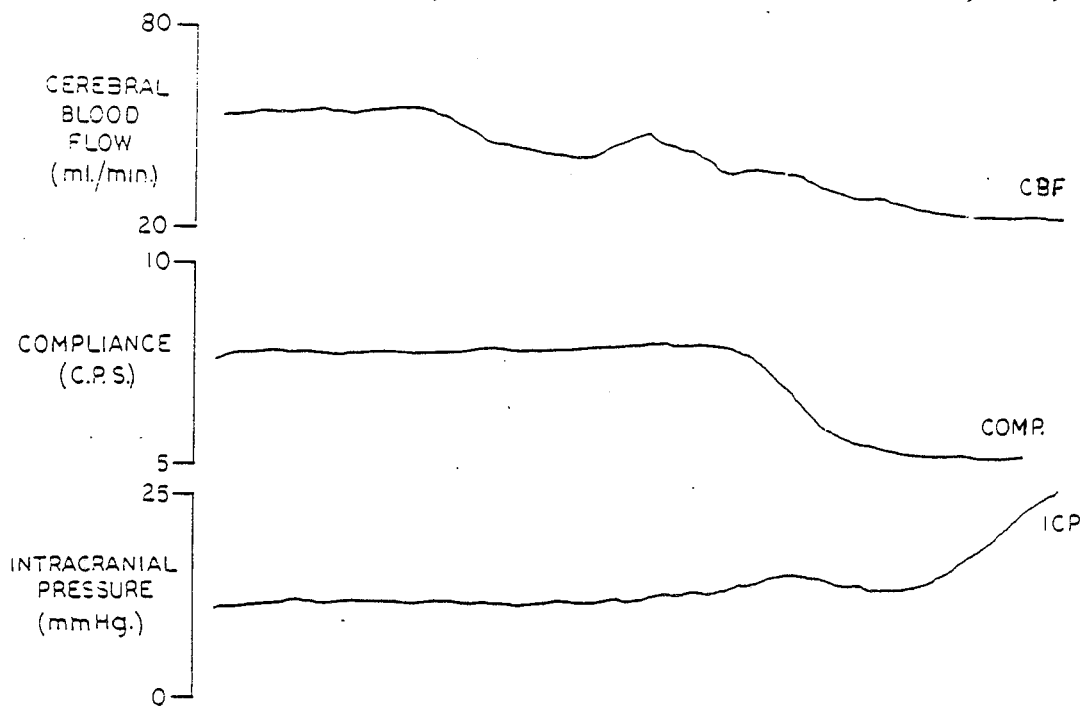
FIG. 5 is a schematic representation of data indicating a physiological state in the brain in which the cerebral blood flow is becoming dangerously low.

Referring to FIG. 5, one sees a situation in which the cerebral blood flow is decreasing with time. When a decrease in cerebral blood flow is followed by a sudden rise in the means intracranial pressure it provides an early warning of dangerously low cerebral blood flow which could lead to ischemia and stroke. The observed drop in the value of cerebral compliance is due to the decreased volume of blood in the brain.

Figure 6:
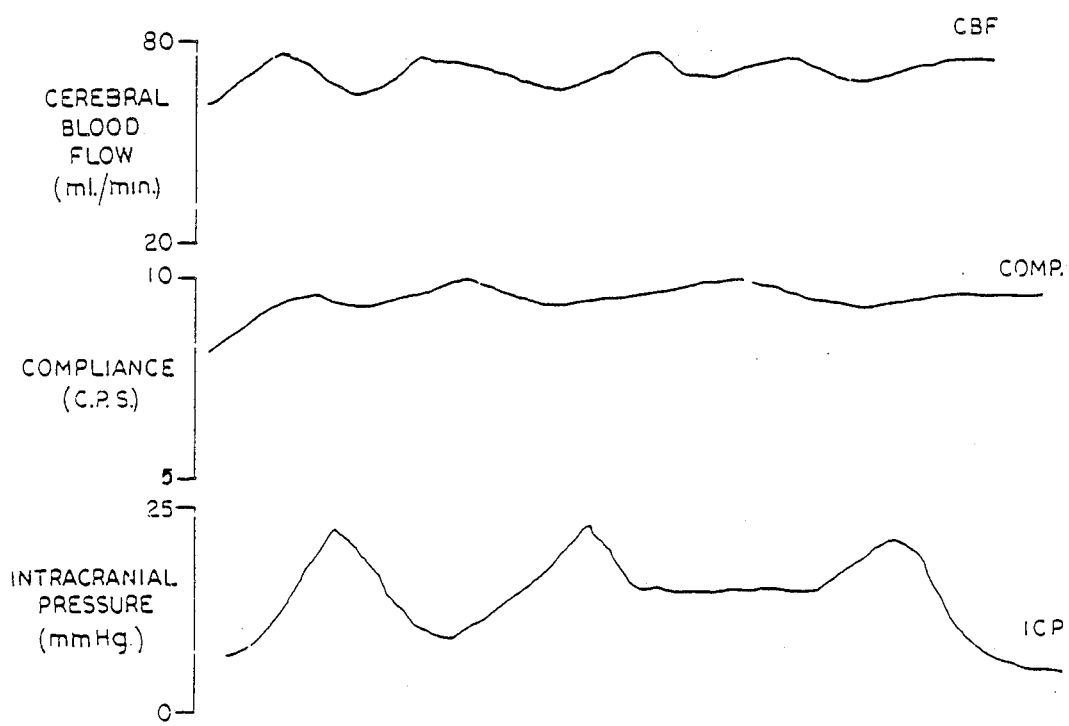
FIG. 6 is a schematic representation of data indicating a physiological state in the brain in which the cerebral blood flow is becoming dangerously high.

A second situation is depicted in the graphs shown in FIG. 6. Here the value of the cerebral blood flow is very high and a condition known as "hyperemia" exists. The high levels of cerebral blood flow increases the "stiffness" of the brain causing the observed values of cerebral compliance to also he high. The intracranial pressure shows variations due to the fact that at high levels of cerebral blood flow it is difficult for the body to properly regulate the intracranial pressure. It is important to detect this condition and distinguish it from the low cerebral blood flow condition in order to apply the appropriate therapy. The therapy for increased levels of cerebral blood flow would attempt to lower the patient's blood pressure in general and the patient's cerebral perfusion pressure in particular.

Figure 7:
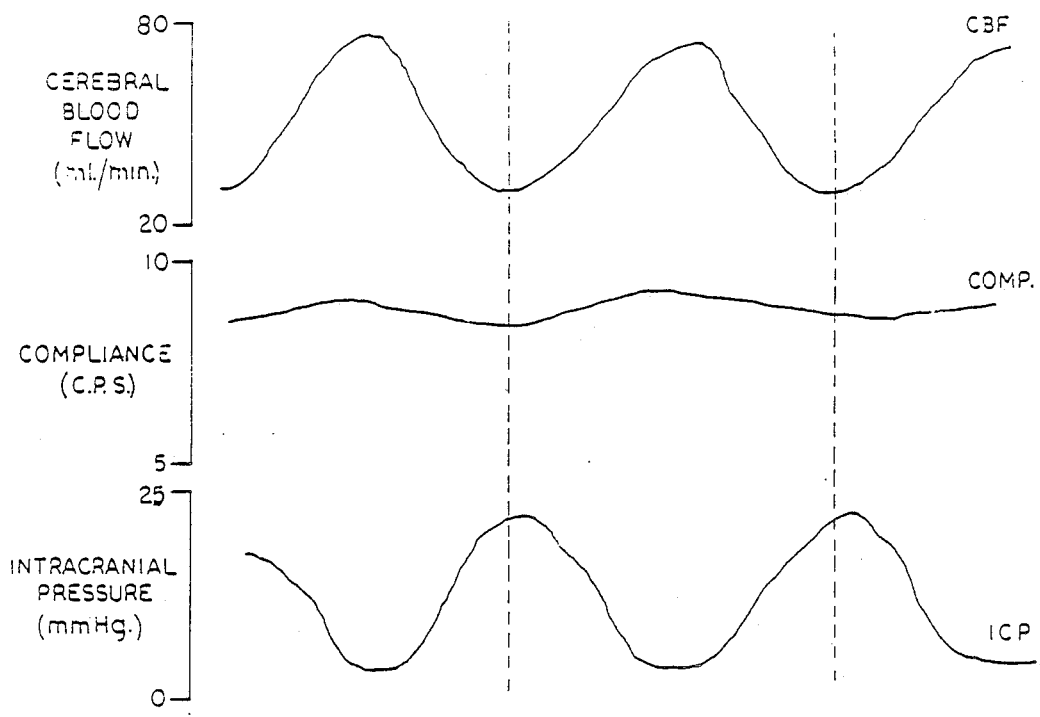
FIG. 7 is a schematic representation of data indicating a physiological state in the brain in which the cerebral blood flow has become unregulated.

FIG. 7 depicts another physiological state in the patient's brain. In this case the patient has lost the capacity to control the cerebral blood flow. The cerebral blood flow is alternately increasing and decreasing with time. This condition may occur in cases of severe brain injury. The intracranial pressure is also fluctuating with time out of phase with the cerebral blood flow. That is, when the intracranial pressure is up, the cerebral blood flow is down, and vice versa. The cerebral blood flow in this condition decreases to dangerously low levels each time the intracranial pressure increases. This is a very bad prognostic sign. Therapy would be directed at stabilizing the fluctuations in the intracranial pressure.

Figure 8:
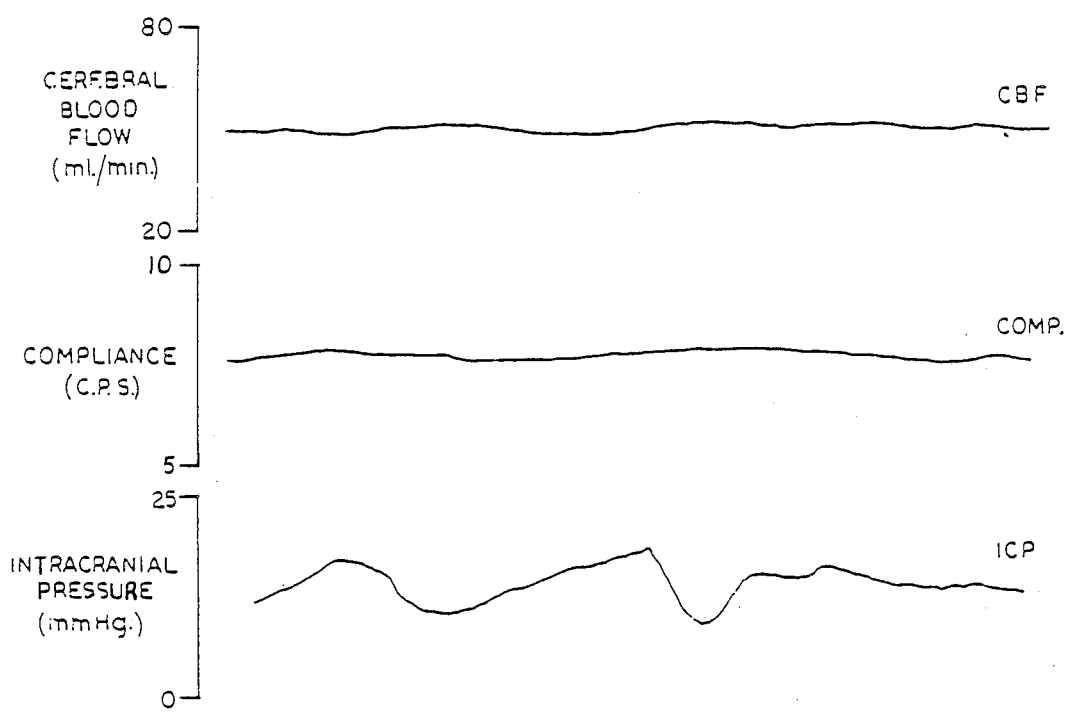
FIG. 8 is a schematic representation of data indicating a physiological state in the brain in which the cerebral blood flow and the cerebral compliance are reasonably well regulated.

The physiological state of the brain depicted in FIG. 8 is one in which the cerebral blood flow is relatively stable as is the cerebral compliance. Although there are some fluctuations in the intracranial pressure, the brain is reasonably well stabilized. This pattern indicated a well compensated injury and a good prognosis for recovery.

Figure 9:
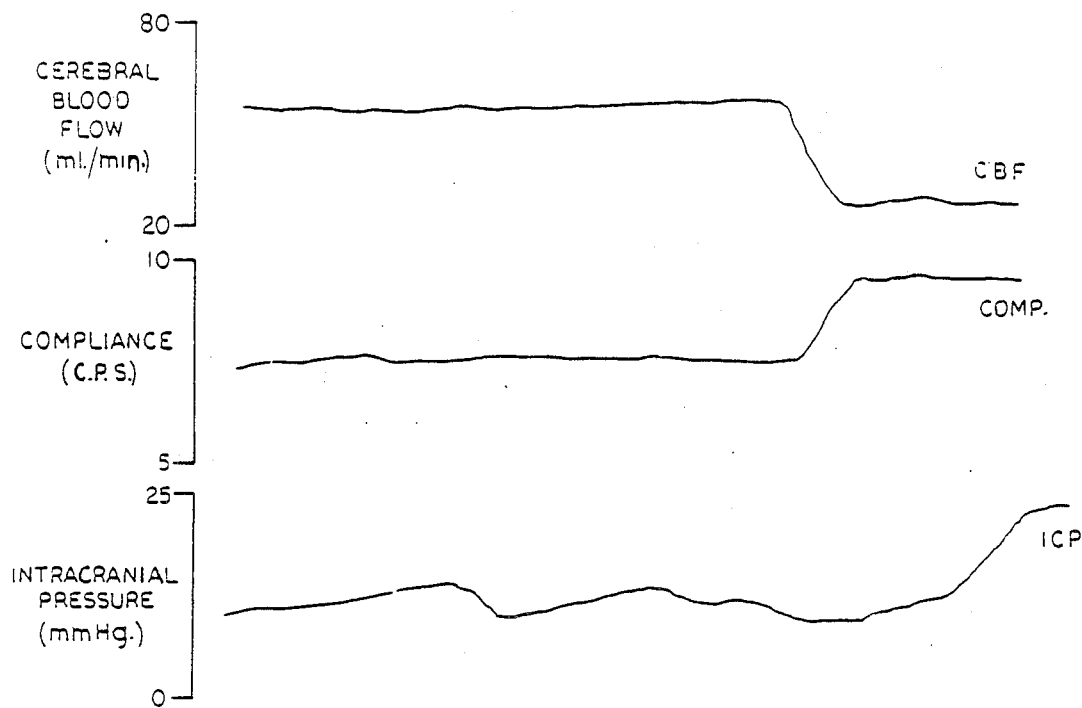
FIG. 9 is a schematic representation of data indicating a physiological state in the brain in which abrupt changes in the cerebral blood flow, cerebral compliance and intracranial pressure indicate the sudden development of a severe problem.

FIG. 9 depicts a physiological state in which there is an acute change of cerebral blood flow and cerebral compliance from previous values. The cerebral blood flow has decreased rather abruptly and the cerebral compliance has increased rather abruptly. The changes in the cerebral blood flow and the cerebral compliance precede the change in the intracranial pressure due to the fact that the increase in the intracranial pressure does not occur until after the body's compensating mechanisms have failed. This pattern indicates the development of a severe problem such as a hematoma postoperative. Early detection of this condition is essential for life preserving measures to be successful.

The examples discussed above illustrate the clinical utility of a continuous on-line real time measurement of the cerebral compliance, cerebral blood flow and the mean intracranial pressure in the diagnosis and treatment of patients with brain disorders or injuries. The invention provides means for obtaining a more accurate diagnosis, means for detecting problems at an early stage of development, means for evaluating the effects of treatment and means for obtaining valuable information for prognostic determinations.

Other forms of pressure sensors may be used to acquire the waveform information for analysis. For example, recordings may be taken from waveform variations in the veins that drain from the brain into the neck. Alternatively, it may be possible to take recordings from waveform variations in the surface of the eye as the eye pulsates in response to fluctuations in pressure within the brain. Techniques such as these would permit a less invasive and more clinically useful monitoring method in that surgery would not be necessary to acquire the intracranial pressure waveform.

Similarly, the methods embodied in the invention may be applied to analyze waveforms from other parts of the body to gain similar types of information. Organs which may be adaptable to the analysis techniques of the invention include the heart, the kidney, the lungs and other organs. For example, the compliance of the heart wall may be determined in a fashion similar to that used to determine the cerebral compliance.

Therefore, it is clear that the invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

10 patient
12 sensor
14 pressure transducer
16 signal monitor
18 electrocardiograph
20 respirator
22 respirator pressure switch
24 respirator gating means
26 analog to digital converter
28 data bus
30 central processing unit
32 video display 34 keyboard
36 printer
37 disc memory
38 data bus
40 parallel interface unit
42 signal line
44 signal line
46 manual dual switch
48 signal line
50 signal line
52 automatic switch
54 manual dual switch

```
c    Main ICP collection program
c
c    ***************************************************************
c                                                                   *
c    Revision History:                                              *
c                                                                   *
c    8-25-83 -AMS- begun revision to improve input parameters,      *
c                  adds Stop, improve graphics                      *
c                                                                   *
c    8-28-83 -AMS- continue revisions - go for sequential scan      *
c                  rearrange stuff                                  *
c                                                                   *
c    9-2-83  -AMS- add triggering, printout                         *
c                                                                   *
c    9-15-83 -AMS- continue revisions, reformat output, etc.        *
c                                                                   *
c    9-19-83 -AMS- change menu, work on triggering                  *
c                                                                   *
c    10-4-83 -AMS- add call to pline - uses Microcompatible         *
c                                                                   *
c    10-10-83 -AMS- changes to ACQN routine - chg to ICP.FOR        *
c                                                                   *
c                  (saved previous version as icpold.exe,for        *
c                                                                   *
c    10-24-83 -JAH- Added FFILL call for spectral plot.             *
c                   Changed default nopts to 128.                   *
c                   Added start up scaling.                         *
c                   Changed WNDOW to sample ICP 4 pts early         *
c                                                                   *
c    11-10-83 -JAH- Added file storage to routine.                  *
c                   Three files are created for each case.          *
c                   (name).ASC for patient information and          *
c                   system configuration.                           *
c                   (name).CEN for centroid information             *
c                   (name).WAV for waveform recordings              *
c                                                                   *
c    12-1-83 -AMS- Add routine for displaying trend on screen       *
c                                                                   *
c    1-8-84  -JAH- Added comment file to store comments             *
c                  separately. Also added detection of              *
c                  significant events, changes in mean              *
c                  values of mean icp, or centroids,                *
c                  resulting in storage of pre- and post-           *
c                  event waveforms. Data is time marked as          *
c                  usual.                                           *
c                                                                   *
c    2-9-84  -AMS- break up into many subroutines                   *
c                                                                   *
c                                                                   *
c                                                                   *
c                                                                   *
c                                                                   *
c                                                                   *
c    ***************************************************************
        integer*1 idata(8,256),idatz(8,256)
        integer*2 data(4,256),datz(4,256)
        dimension xdata(256),ydata(256),bufr(5),bufr1(5),zdata(256)
        dimension xodata(256)
      1,ekgdat(256),ekgth(2),icon(32),rcon(32),trndc(610,6),centm(
      2,iyca(6),iypcs(20)
        character*30 answer,name,date,coment,substo,answ1,ans,p1,p2,p3
```

```
     1 , p1a,p2a,p3a,ans2,ans21,p4,p4a,wind,fname1
     2, name2,name1,ncnt,fname,gstrng
       equivalence (idata,data),(iyear,icon(1)),(month,icon(2))
     1,(iday,icon(3)),(ihrs,icon(4)),(mins,icon(5)),(israte,icon(6))
     2,(iloop,icon(7)),(inum,icon(8)),(ichn,icon(9))
     3,(nopts,icon(10)),(itrch,icon(11)),(idelay,icon(12))
     4,(icmx,icon(13)),(isave,icon(14)),(cent1,rcon(1))
     5,(centh1,rcon(2)),(cent12,rcon(3)),(centh2,rcon(4))
     6, (trglvl,rcon(5)),(idatz,datz),(iclp,iyca(6)),(clbmx,rcon(11))
     7,(itrflg,icon(15)),(num,icon(16)),(imax,icon(17))
     8,(mxartc,icon(18)),(xminf,rcon(6)),(artfac,rcon(7))
     9,(dcent1,rcon(8)),(dcent2,rcon(9)),(dmean,rcon(10))
     *,(itrpl,icon(19)),(ymax2,rcon(12)),(ymax1,rcon(13))
     *,(ymax4,rcon(14)),(iypos(1),iy),(iypos(2),iy1)
     *,(iypos(3),iy2),(ymax,rcon(15))
       data imax/256/
c
c  NOTE!  change imax if you change size of arrays idata,data and xdata
c
c
c  array useage;
c
c     idata - initial data acquisition
c     idatz - zero buffer
c     xdata - real part of data to FFT
c     ydata - complex part of data to FFT
c     bufr  - parameter buffer to ADC routine
c     bufr1 - second parameter buffer to ADC routine
c     (character*30) - various string variables
c
c
       data israte/200/
     1,iloop/-2/,inum/2/,ichn/0/,answer/"Go"/
     2,nopts/256/,lu/4/,bufr/128.,10000.,.2,3.,0./,itrch/2/,trglvl/120./
     3,bufr1/128.,10000.,4.,15.,0./,itrflg/-2500/,idelay/8/,lu4/2/
     4,ix/1/,iy/140/,iy1/80/,iy2/5/,kolor/7/,ymax/3000./,ymax1/6000./
     5,mode2/2/,mode6/6/,ymax2/8./,num/128/,p1/"Y"/,p2/"Y"/,p3/"Y"/
     6,scl/4./,micp/10/,icmx/10/,p4/"Y"/,n1/100/,nplot/256/,wind/"Y"/
     7,fname/""/,ans2/"Y"/
     8,icomnt/0/,gstrng/"G"/
     9,itrnd/0/,ifull/0/,nplt/600/,iyca/160,10,100,50,0,1/
     *,artfac/200./,nmax/600/,clbmx/199./,itrpl/2/
     *,xminf/200./,isave/100/,dcent1/.5/,dcent2/1./,dmean/10./
     *,mxartc/10/,ifirs/0/
     *,datmn1/10000./
c
c
       call inprt(name1,name2,fname)
c
c
.4     write(1,35)LU,lu4
 35    format(' Print to (',i1,' - 1=console, 4=printer
     1, 5=none)? with individual printing 1=on,2=off (',i1,')? '$
       read(1,125)lu1,lu5
.25    format(2i0)
       if (lu1 .ne. 0)lu=lu1
       if (lu1 .eq. 5)lu=0
       if (lu5 .ne. 0) lu4=lu5
       call gtime(ihrs,mins,isec,icsec)
       call gdate(month,iday,iyear)
       if (lu .ne. 0)
     1 write(LU,45)ihrs,mins,month,iday,iyear,name2,name1,fname
 45    format('1',///,25x,'Trinity Computing Systems'
     1,//,12x,'ICP Analysis by Means of the Power Spectrum'
     2,/,12x,'Acquisition started: ',i2,':',i2,' on ',i2,'/',i2,'/',i4
     3,/,12x,'Patient: ',a0,', ',a0,'  file: ',a0)
```

```
 47        format(2x,'          CBF              COMPLIANCE')
 46        format(2x,'Centroid1 Peak Frq.  Centroid2  Peak Frq.',6x,
      1    'Mean ICP')
466        format(2x,70('-')/)
c
c  get scaling parameters for display, etc.
c
           ifirst=0
  5        call qrmode(mode,nccl)
           if (mode .ne. 2) call qsmode(mode2)
           write(1,50)israte,iloop,inum,ichn
 50        format(//,' Current values are:'
      1    ,' Sample rate= ',i4,/' Number of repetitions (-2=inf.loop):'
      2    ,i3/' no. channels=',i2,', 1st ch=',i2 $
           write(1,51)nopts,trglvl,itrch,idelay
      1,   bufr(3),bufr(4),bufr1(3),bufr1(4)
 51        format(' , points/ch=',i4,/' Trig. level=',f9.2,', channel=',i1,
      1    , ', waiting time for trigger: ',i2,"S'
      2    /' windows: - ',f4.1,' low, ',f4.1,' high, 2nd: ',f4.1,' to ',f4.1)
           call check(3,ichk)
           if (ichk.eq.1) goto 99
           write(1,41)
 41        format(//2x,'Set acquisition switch to ON position'/)
 99        if (ifirst.ne.0)goto102
           write(1,101)
101        format(//' Calibrate next.  Hit RETURN key when ready.' $
           read(1,65)ianswl
           goto 70
100        call qsmode(mode2)
102        ifirst=1
 40        write(1,60)answer
 60        format(/3x,'Now what?'//6x,'Reset parameters,'/6x,'Comments,'
      1    /6x,'Trend plot,'
      2    /6x,'Help,'/6x,'End the program,'
      3    /3x,'or Go to data acquisition (',a0,')? ' $
           read(1,65)answl
 65        format(a20)
c
           if (klen(answl) .gt. 0) answer=answl
           if (substg(answer,1,1) .eq. "R") goto 95
           if (substg(answer,1,1) .eq. "G") goto 117
           if (substg(answer,1,1) .eq. "E") goto 9999
           if (substg(answer,1,1) .eq. "D") goto 85
           if (substg(answer,1,1) .eq. "H") goto 75
           if (substg(answer,1,1) .eq. "C") goto 660
           if (substg(answer,1,1) .eq. "t") goto 650
           if (substg(answer,1,1) .eq. "T") goto 650
           if (substg(answer,1,1) .eq. "c") goto 660
           if (substg(answer,1,1) .eq. "h") goto 75
           if (substg(answer,1,1) .eq. "d") goto 85
           if (substg(answer,1,1) .eq. "r") goto 95
           if (substg(answer,1,1) .eq. "g") goto 117
           if (substg(answer,1,1) .eq. "e") goto 9999
           goto 40
c
c - - - - - - - - - - - - - - - - - - - - - - - -
c
660        call comm(icomnt,LU)
           goto 40
c
 75        call help
           goto 40
c
650        call trnd(trndc,ifull,itrnd,fname,clbmx,iyca)
           goto 40
```

```
810       call analp(icon,rcon)
          goto 40
c
c
c  section to setup debug conditions
c
85        write(1,8501)idebug
8501      format(' Debug? 1=yes, -1=no (',i2,')? ' $
          read (1,8502)idbg
8502      format(i0)
          if (idbg .ne. 0) idebug=idbg
          goto 40
c
c
95        write(1,855)ans
855       format(/3x,'Select one of the following options:'/
     1 /6x,'Window mode,'/6x,'Calibrate,'/6x,'Intervals for documenting'
     2 /6x,'Display parameters,'/6x,'Sample rate (total),'
     3 /6x,'Number of points, ADC parameters,'/6x,'Frequency of '
     4,'centroid limits,'/3x,'or All of the above (',a0,')? ',11x $
          read(1,65)answ1
          iall=0
          if (klen(answ1) .gt. 0) ans=answ1
          if (substg(ans,1,1) .eq. "a") iall=1
          if (substg(ans,1,1) .eq. "A") iall=1
          if (substg(ans,1,1) .eq. "w") goto 666
          if (substg(ans,1,1) .eq. "W") goto 666
          if (substg(ans,1,1) .eq. "d") goto 720
          if (substg(ans,1,1) .eq. "D") goto 720
          if (substg(ans,1,1) .eq. "C") goto 700
          if (substg(ans,1,1) .eq. "c") goto 700
          if (substg(ans,1,1) .eq. "S") goto 820
          if (substg(ans,1,1) .eq. "s") goto 820
          if (substg(ans,1,1) .eq. "N") goto 830
          if (substg(ans,1,1) .eq. "n") goto 830
          if (substg(ans,1,1) .eq. "F") goto 840
          if (substg(ans,1,1) .eq. "f") goto 840
          if (substg(ans,1,1) .eq. "A") goto 830
          if (substg(ans,1,1) .eq. "I") goto 810
          if (substg(ans,1,1) .eq. "i") goto 810
          if (substg(ans,1,1) .ne. "a") goto 95
c
c
666       write(1,6666)wind
6666      format(' Windowing ON (',a0,')? :'$
          read(1,65)answ1
          if (klen(answ1) .eq. 0) goto 6667
          wind="N"
          if(substg(answ1,1,1).eq."Y") wind="Y"
          if(substg(answ1,1,1).eq."y") wind="Y"
6667      if (iall.ne.1) goto 40
c
c
830       call setup(icon,rcon,iall)
          goto 40
c
c now set up new plotting factors
c
c now new section
c which displays and asks for stuff
c
700       call check(10,icomnt)
          icomt1=icomnt
          call incnt(israte)
          write(1,7000)
7000      format(' (collecting sample data set now) - please wait)')
```

```
              call acqn (idata,inum,ichn,nopts,idebug)
7001          write(1,701)micp
701           format(' Enter the mean ICP from monitor: (',i3,')? ' $
              read (1,702)micp1
702           format(i0)
              if (micp1 .gt. 0) micp=micp1
              sum=0.
              do 703 i=1,nopts
              xdata(i)=float(data(1,i))
c
c   now debug
c
c             write(1,7021)xdata(i)
7021          format(f6.3)
c
703           sum=sum+xdata(i)
              avg=sum/nopts
c
c debug
c
              write(1,7022)avg,sum,nopts
7022          format(2x,'avg=',f9.2,', sum=',f9.2,', nopts=',i4)
c
              write(1,704)
704           format(' Now zero the pressure reading, then return')
              write(1,7041)
7041          format (6x,'(If zero unavailable, enter 999)' $
              read(1,702)izero
              zicp=0
              avgz=0
              if (izero .eq. 999) goto 705
              if (izero .ne. 0) zicp=izero
              call acqn(idatz,inum,ichn,nopts,idebug)
              sum=0.
              do 710 i=1,nopts
              ydata(i)=float(datz(1,i))
710           sum=sum+ydata(i)
              avgz=sum/nopts
c
c  the fudge factor is to convert absolute computer units
c  to mm Hg. When it is established that a zero value can be
c  read in, change micp to (micp-zicp)
c
705           fudge=abs((micp-zicp)/(avg-avgz))
c this is supposed to convert values to mm,
c assuming that there is no offset when mm=0
c
720           write(1,721)scl
721           format(' Enter scale for ICP (',f4.0,'mm)? ' $
              read(1,110)scl1
              if (scl1 .gt. 0) scl=scl1
              rcon(15)=scl*10/fudge
              rcon(13)=rcon(15)*2
              rcon(12)=rcon(15)/2
              iyact=iy1-avg*199./rcon(15)
              call qrmode(imod,icol)
              if ((imod .ne. 6) .or. (substg(ans2,1,1) .eq. "n")
     1        .or. (substg(ans2,1,1) .eq. "N")) call qsmode (mode6)
              nplot=nopts
              call pline (ix,iyact,xdata,kolor,nopts,ymax,nplot)
              write(1,730)ans2
730           format(' Is this displayed ok -Yes,change Gain or Mean,No (',a0,')? '
              read(1,65)ans21
              if (klen (ans21) .gt. 0)ans2=ans21
              if (substg(ans2,1,1) .eq. "y") goto 805
              if (substg(ans2,1,1) .eq. "Y") goto 805
```

```
              if (substg(ans2,1,1) .eq. "g") goto 720
              if (substg(ans2,1,1) .eq. "G") goto 720
              if (substg(ans2,1,1) .eq. "M") goto 7001
              if (substg(ans2,1,1) .eq. "m") goto 7001
              if (substg(ans2,1,1) .eq. "n") goto 700
              if (substg(ans2,1,1) .eq. "N") goto 700
              goto 700
c
805           if (ifirst .eq. 0) goto 100
815           call dsplp(icon,rcon,iyca,p1,p2,p3,p4,iy,iy1,iy2)
c
c
c
820           write(1,112)israte
112           format(2x,'Enter sample rate (200 Hz max): (',i4,' Hz) - '$
              read(1,114)israt1
              if (israt1 .ne. 0) israte=israt1
              n1=israte/inum
c
c  this sets up the pointer for starting window search -
c  calculated as: 300 ms/(ms per point)=300/(1000*inum ch/israte Hz)
c
c
              if (iall .eq. 0) goto 40
114           format(i0)
c  Now set up first centroid window
c
840           write(1,96)bufr(3)
96            format(' 1st centroid window: beginning (',f4.1,')?' $
              read(1,110)beg
110           format(f0.0)
              write(1,97)bufr(4)
97            format(' and ending  (',f4.1,')? '$
              read(1,110)end
              if (beg .ne. 0.) bufr(3)=beg
              if (end .ne. 0.) bufr(4)=end
c
c  Now do second centroid window
c
              write(1,961)bufr1(3)
961           format(' 2nd centroid window: beginning (',f4.1,')?' $
              read(1,110)beg
              write(1,97)bufr1(4)
              read(1,110)end
              if (beg .ne. 0.) bufr1(3)=beg
              if (end .ne. 0.) bufr1(4)=end
c             write(1,98)
c
              bufr1(5)=bufr(5)
              goto 40
c
c  now start the loop business
c
117           if (num .gt. nopts/2) num = nopts/2
              bufr(1)=nopts
              bufr(2)=inum*10.**6/israte
c
c  first print out basic parameters
c
              call check(3,ichk)
              if (ichk.eq.1) goto 1192
              write(1,1191)
1191          format(//2X,'Set acquisition switch ON to continue'/)
              goto 40
1192          if (lu .ne. 0)
     1        write(lu,119)nopts,bufr(2)/1000.,bufr(3),bufr(4),bufr1(3),bufr1(4)
```

```
119     format(/' With ',i3,' points and a sampling interval of '
       1, f6.0,' mS/channel,'/' the centroid windows used are: '/
       2, 6x,'Window 1 from ',f5.2,' to ',f5.2,', Window 2 from '
       3, f5.2,' to ',f5.2,//)
        if (lu .eq. 0) goto 1194
        if (substg(wind,1,1) .eq. "Y")write(lu,1193)
1193    format(' Data is now windowed...'/)
        write(lu,47)
        write(LU,46)
        write(lu,466)
c
c set up loop count: -1 to quit, -2 for infinite looping
c
1194    write(1,115)iloop
115     format(//2x,'<+n> # to Loop: <-1> to menu, <-2> infinite (',i3,'): '
        read(1,114)iloop1
        if (iloop1 .eq. -1) goto 40
        if (iloop1 .ne. 0) iloop=iloop1
c
c
c   Save acquisition parameters
c
        centl1=bufr(3)
        centh1=bufr(4)
        centl2=bufr1(3)
        centh2=bufr1(4)
        write(5,endfile=10000,errexit=10010)name2,name1
        write(5,endfile=10000,errexit=10010)(icon(i),i=1,32)
        write(5,endfile=10000,errexit=10010)(rcon(i),i=1,32)
c
        iscnt=1
        igate1=0
        iresp1=0
        if (iloop .eq. -2) goto 1195
        do 80 jj=1,iloop
c
c   A-D section
c
c
c   call trigger if desired
c
1195              call check(3,istart)
            call gdate(imonth,iday1,iyear)
               if (istart .eq. 0)
     1         call pmean(iday1,lu,icntm,centm,icount,icmx,iferr)
               if(iferr.eq.1) goto 10000
               if(iferr.eq.2) goto 10010
               if (istart.eq.0) goto 5
               call check(8,igate)
               if ((igate .eq. igate1) .and. (igate .eq. 0)) goto 1198
               call gtime(ihrs,mins,isec,icsec)
               if (igate .eq. 1) goto 1197
               call pmean(iday1,lu,icntm,centm,icount,icmx,iferr)
               if(iferr.eq.1) goto 10000
               if(iferr.eq.2) goto 10010
               if (lu .ne. 0) write(lu,11952)ihrs,mins
               igate1=igate
               goto 1198
1197           call check(9,iresp)
               if ((igate .eq. igate1) .and. (iresp1 .eq. iresp)) goto 1198
               call pmean(iday1,lu,icntm,centm,icount,icmx,iferr)
               if(iferr.eq.1) goto 10000
               if(iferr.eq.2) goto 10010
               igate1=igate
11960          if ((iresp .eq. 0) .and. (lu .ne. 0))write(lu,11951)ihrs,mins
               iresp1=iresp
```

```
                    if ((iresp .eq. 1).and.(lu .ne. 0)) write(lu,11953)ihrs,mins
11953               format(/2x,'Respiration gating on for inspiration at '
     1,             i2,':',i2/)
11951               format(/2x,'Respiration gating on for expiration at '
     1,             i2,':',i2/)
11952               format(/2x,'Respiration gating OFF at ',i2,':',i2/)
1198                itrfl1=itrflg
c
c   this next to check for comment
c
                    call check(10,icomnt)
                    if (icomnt .eq. icomt1) goto 1199
                        call comm (icomnt,lu)
                        goto 1195
c
c   now trigger
c
1199                if (trglvl .ge. 0) call aqtrg(itrch,trglvl,itrfl1)
                    if (itrfl1 .eq. 1) goto 5
c
c
                    call incnt(israte)
c       this subroutine is used to initialize counter for ADC
c
c   now call acquisition routine:
c
                    call acqn(idata,inum,ichn,nopts,idebug)
c
c
c   Now display data
c
                    if (idebug .eq. 1) call qsmode(mode2)
                    sum=0
                    sumekg=0
                    iart=0
                    datmin=datmn1
                    do 600 i=1,nopts
c
c   Scale the data to real volts
c
                        xdata(i)=float(data(1,i))
                        sum=sum+xdata(i)
                        ekgdat(i)=float(data(2,i))
                        sumekg=sumekg+ekgdat(i)
                        ydata(i)=0.
c
c   now artifact rejection stuff:
c
                        if (xdata(i) .lt. datmin) datmin = xdata(i)
                        if (ekgdat(i) .lt. (avgekg-artfac)) iart=iart+1
c
                        if (idebug .ne. 1) goto 600
                        write(1,4001)idata(1,i),data(1,i),idata(5,i),data(1,i)
4001                    format(z2,'-',z6,', ',z4,': ',i7)
600                 continue
c
c   calculate the offset from the average for the icp
c
                    avgekg=sumekg/nopts
                    avg=sum/nopts
                    avgm=avg*fudge
                    iyact=iy-avg*199./ymax
                    iyact4=iy-avg*199./ymax4
c
c   now check to see if artifact is present:
```

```
c     temporarily move to after plot
c     now plot the data with new call to pline
c              call qrmode(imod,icol)
               if (idebug .ne. 1) goto 610
               pause
610            call qsmode (mode6)
               if (substg(p1,1,1) .eq. "Y")
     1           call pline (ix,iyact,xdata,kolor,nopts,ymax,nplot)
               if (substg(p2,1,1) .ne. "Y") goto 1850
               call pline(ix,iy1,ekgdat,kolor,nopts,ymax1,nplot)
               ekgth(1)=trglvl
               ekgth(2)=ekgth(1)
               npt=2
               call pline(ix,iy1,ekgth,kolor,npt,ymax1,2)
               ekgth(1)=0
               ekgth(2)=0
               call pline(ix,iy1,ekgth,kolor,npt,ymax1,2)
c
1850     continue
c
c   temporary residence of artifact suppression
c
c        write(1,18491)datmin,avg,xminf,iart,mxartc
18491    format(2x,'datmin=',f9.2,', avg=',f9.2,
     1   ', xminf=',f9.2,', iart=',i6,', mxartc=',i6)
               if (datmin .lt. (avg-xminf)) goto 1195
               if (iart .gt. mxartc) goto 1195
c
c
c now jump to new routine to window the data
c
         if (substg(wind,1,1) .ne. "Y") goto 1860
         call wndow(xdata,ekgdat,nleft,nopts,n1,trglvl)
         if ((nleft .gt. 0) .or. (lu .eq. 0)) goto 360
         if (nleft .eq. -1) write(lu,3601)
c        if (nleft .eq. -2) write(lu,3602)
         goto 203
3601     format(' Window failed on QRS level')
3602     format(' Window failed on ICP level')
c
360      if (substg(p4,1,1) .eq. "Y")
     1      call pline(ix,iyact4-10,xdata,kolor,nopts/2,ymax4,nleft+4)
c
C Now call routine to perform xform
C
c
1860     if(iscnt.ne.isave) goto 1865
         write(7,endfile=10000,errexit=10010)ihrs,mins
         write(7,endfile=10000,errexit=10010)(xdata(i),i=1,nopts)
         iscnt=0
1865     iscnt=iscnt+1
         do 1890 iz=1,nopts
1890     xodata(iz)=xdata(iz)
         if(icntm.ne.0) goto 1880
         do 1870 iz=1,nopts
1870     zdata(iz)=xdata(iz)
1880           invert=0
               nump=nopts
               call fft84(invert,nump,xdata,ydata)
c
C
C Now output the results of the computation
C
               do 200 i=1,nopts/2
                 dmag=sqrt(xdata(i)**2+ydata(i)**2)
                 xdata(i)=dmag
```

```
              if(dmag.le.0) dmag=.00001
              ekgdat(i)=alog10(dmag)
c
200           continue
c
c
        if (substg(p3,1,1) .ne. "Y")goto2010
        call pfill (ix,iy2,ekgdat(2),kolor,num-1,ymax2,num-1)
c
c  now continue to centroid subroutine
c
2010    bufr1(1)=bufr(1)
        bufr1(2)=bufr(2)
c  (this last sets the routine to write out results)
c
        call centr(xdata,bufr,cent,pspec,pfreq)
        call centr(xdata,bufr1,cent1,pspec1,pfreq1)
c
        if (lu4 .eq. 1)write(LU,202)cent,pfreq,cent1,pfreq1,avgm
202     format(' C=',f5.2,', pk=',f5.2,',   C2=',f5.2,', pk2=',f5.2
     1,',   ICP = ',f6.2,' mm')
        if (lu4 .eq. 2)write(1,202)cent,pfreq,cent1,pfreq1,avgm
        centm(1)=cent+centm(1)
        centm(3)=cent1+centm(3)
        centm(2)=centm(2)+pfreq
        centm(4)=centm(4)+pfreq1
        icntm=icntm+1
        centm(5)=centm(5)+avgm
c
c
c  now save in an array for on-line plotting of each point in trend
c
        IF ((itrpl .eq. 2) .and. (icntm .ge. icmx)) itrnd=itrnd+1
        if (itrpl .eq. 1) itrnd=itrnd+1
        if (itrnd .gt. 600)ifull=1
        if (itrnd .gt. 600)itrnd=1
        if (itrpl .ne. 1) goto 20335
        trndc(itrnd,1)=cent
        trndc(itrnd,2)=pfreq
        trndc(itrnd,3)=cent1
        trndc(itrnd,4)=avgm
        trndc(itrnd,5)=0
        call gtime(ihrs,mins,isec,icsec)
        if (int(mins/10) .eq. minold) goto 2034
        trndc(itrnd,5)=10
        minold=int(mins/10)
        goto 2034
c
c  this next is the mean value save for trend, prev saves every one
c
20335   IF (icntm .lt. icmx) goto 2034
        trndc(itrnd,1)=centm(1)/icntm
        trndc(itrnd,2)=centm(2)/icntm
        trndc(itrnd,3)=centm(3)/icntm
        trndc(itrnd,4)=centm(5)/icntm
        trndc(itrnd,5)=0
        call gtime(ihrs,mins,isec,icsec)
c
c  DATA SAVE on event
c
        if(ifirs.ne.0) goto 33000
        ifirs=1
        goto 30000
33000   if (abs(trndc(itrnd,1)-ocent1).gt.dcent1) goto 30020
        if (abs(trndc(itrnd,3)-ocent2).gt.dcent2) goto 30020
        if (abs(trndc(itrnd,4)-omean).gt.dmean) goto 30020
```

```
              goto 30000
30020         write(7,endfile=10000,errexit=10010)iohrs,moins
              write(7,endfile=10000,errexit=10010)(zdata(i),i=1,nopts)
              write(7,endfile=10000,errexit=10010)ihrs,mins
              write(7,endfile=10000,errexit=10010)(xodata(i),i=1,nopts)
30000         if (ihrs .eq. ihrold) goto 2034
              trndc(itrnd,5)=10
              ihrold=ihrs
c
c finished array save
c
2034          IF (icntm .lt. icmx) goto 2035
              call pmean(iday1,lu,icntm,centm,icount,icmx,iferr)
c
c   Data save and time save for later waveform storage
c
              iohrs=ihrs
              moins=mins
              ocent1=trndc(itrnd,1)
              ocent2=trndc(itrnd,3)
              omean=trndc(itrnd,4)
                  if(iferr.eq.1) goto 10000
                  if(iferr.eq.2) goto 10010
2035          ICOUNT=ICOUNT+1
              IF (ICOUNT .LT. 100) GOTO 203
              call gtime(ihrs,mins,isec,icsec)
              if (lu .ne. 0) write(lu,204)ihrs,mins
204           format(40x,'Time:',i2,':',i2)
              icount=0
:
203           if (iloop .eq. -2) goto 1195
30            continue
              goto 5
10000         write(1,10001)
10001         format(1x,'End of file occurred')
              goto 9999
10010         write(1,10011)
10011         format(1x,'File error occurred')
9999          if (ioclos(5)) write(1,99991)
              if (ioclos(6)) write(1,99992)
              if (ioclos(7)) write(1,99993)
              if (ioclos(8)) write(1,99994)
99991         format(1x,'Ascii file close error!')
99992         format(1x,'Centroid file close error!')
99993         format(1x,'Waveform file close error!')
99994         format(1x,'Comment file close error!')
              call qrmode(mode,ncol)
              if (lu .eq. 4) write (lu,9990)
9990          format('1')
              if (mode .ne. 2) call qsmode(mode2)
              stop
              end begin new subroutine section

- - - - - - - - - - subroutine inprt(name1,name2,fname)

subroutine to initialize printout, files with patient name
and to set up files for: basic parameters (*.asc - 5),
centroid info (*.cen - 6), waveforms (*.wav - 7), and
comments (*.com - 8)

character*30 fname1,fname2,fname3,fname4,name1,name2,ncnt
     1,fname,substg
```

```
        data fname2/""/,fname4/""/,fname1/""/
     8, fname3/""/,ncnt/"0123456789"/
c initialize printout
c
        write(1,10)
10      format(1x,'Enter patient name')
        write(1,13)
13      format(1x,'Last name:  '$
        read(1,11000)name2
        write(1,104)
104     format(1x,'First name: '$
        read(1,11000)name1
11000   format(a0)
c
c File open section
c
        nf1=1
        nf2=2
11      call addstg(fname,substg(name2,1,4),substg(ncnt,nf1,nf1)
     1 ,substg(ncnt,nf2,nf2))
        call addstg(fname1,fname,".asc")
        if (iolook(0,fname1)) goto 121
        goto 12
c
c  file exists, create new one
c
121     if(nf2.lt.10)nf2=nf2+1
        if(nf2.eq.10)nf1=nf1+1
        if(nf2.eq.10)nf2=1
        call setlen.fname1,0)
        call setlen(fname,0)
        if (nf.lt.100) goto 11
        write(1,113)
113     format(1x,'Out of file names')
        goto 9999
12      call addstg(fname2,fname,".cen")
        call addstg(fname3,fname,".wav")
        call addstg(fname4,fname,".com")
        write(1,200)fname
200     format(2x,'creating file set: ',a0)
        if(iowrit(5,0,0,fname1)) goto 141
        if(iowrit(6,0,0,fname2)) goto 141
        if(iowrit(7,0,0,fname3)) goto 141
        if(iowrit(8,0,0,fname4)) goto 141
        return
141     write(1,1141)
1141    format(1x,'error in opening files')
        goto 9999
c
c  end of file setup stuff
        return
9999    stop
        end
c
c - - - - - - - - - - - - - - - - - - - - - - - - -
c
        subroutine trnd(trndc,ifull,itrnd,fname,clbm,iyca)
c
c  this subroutine is to plot the on-line version of the trend
c
        dimension trndc(610,6),iyca(6),trndp(600)
        character*30 fname
c
        data iclor/7/,nmax/600/,mode2/2/,mode/6/
c section to plot out trend on screen
```

```
650     nplt=600
        call qsmode(mode6)
        if (ifull .eq. 0) nplt=itrnd
        write(1,600)fname
600     format(1x,'Data filed in: ',a0)
c
        do 655 i=1,4
c
c   now calculate the max/min to get value for ymx
c
        tmx=-1000.
        tmn=1000.
        do 6501 j=1,nplt
        avgtrn=avgtrn+trndc(j,i)
        if (trndc(j,i) .gt. tmx) tmx=trndc(j,i)
6501    if (trndc(j,i) .lt. tmn) tmn=trndc(j,i)
        ymx=5*(tmx-tmn)
        if (ymx .lt. 5) ymx=5
        if (i .eq. 2)  ymx=ymx*3
        avgtrn=avgtrn/nplt
        if (i .ne. 2) write(1,6502)i,avgtrn
        if (i .eq. 2) avgtr2=avgtrn
        do 6503 j=1,nplt
6503    trndp(j)=trndc(j,i)-avgtrn
        call pline(ix,iyca(i),trndp,kolor,nmax,ymx,nplt)
655     avgtrn=0
6502    format(58x,'Trnd ',i1,' mean is: ',f6.2//////)
        i2=2
        write(1,6502)i2,avgtr2
c
        call pline(ix,iyca(6),trndc(1,5),kolor,nmax,clbmx,nplt)
c
c this plots the time at which the hours change as a vert. bar
c from the bottom of the screen
c
c this next is a dummy read to allow user time to look at plot
c before continuing
c
        read(1,65)date
65      format(a20)
        call qsmode(mode2)
        return
        end
c
c - - - - - - - - - - - - - - - - - - - - - - - -
c
        subroutine comm (icomnt,LU)
c
c  this routine is to enter comments
c
        character*70 commnt
c
        data mode2/2/
c
c comment section
c
660     icomt1=icomnt
        call qrmode(mode,ncol)
        if(mode.ne.2) call qsmode(mode2)
c
        write(1,67)
67      format(' Enter annotation for record: ' $
        read(1,68)commnt
68      format(a70)
        call ehtime(ihrs,mins,isec,icsec)
        if (lu .ne. 0)
      1 write(lu,69)ihrs,mins,commnt
        write(8,endfile=10000,errexit=10010)ihrs,mins,commnt
69      format(/10x,'Note at ',i2,':',i2,' - ',a0/)
        return
```

```
c
c  error section
c
10000   write(1,10001)
10001   format(1x,'End of file occurred')
        goto 9999
10010   write(1,10011)
10011   format(1x,'File error occurred')
9999    if (ioclos(5)) write(1,99991)
        if (ioclos(6)) write(1,99992)
        if (ioclos(7)) write(1,99993)
        if (ioclos(8)) write(1,99994)
99991   format(1x,'Ascii file close error!')
99992   format(1x,'Centroid file close error!')
99993   format(1x,'Waveform file close error!')
99994   format(1x,'Comment file close error!')
        call qrmode(mode,ncol)
        if (lu .eq. 4) write (lu,9990)
9990    format('1')
        if (mode .ne. 2) call qsmode(mode2)
        stop
        end
c
c
c -  -  -  -  -  -  -  -  -  -  -  -  -  -  -  -  -  -  -  -
c
        subroutine help
c
c  Help section
c
75      write(1,76)
        write(1,77)
        write(1,78)
        write(1,79)
76      format(//2x,'This program acquires 2 or more channels of data '
     1, ' using an A/D module.')
77      format(2x,'Connect the cable from the pressure '
     1, 'monitor to the input marked ICP, and'/2x,'the cable from '$
78      format(' the EKG monitor to the input marked EKG.  A second pressure
     4, /,2x,'monitor can be connected to the Ext input.  Connect the '
     5, 'air hose to the'/2x,'respirator to permit sampling at the ' $
79      format(' same point in the respiratory cycle.',
     1/ ' Set the trigger ON and to GATED for this action.'//
     2  2x,'Maximum sampling rate '
     3, 'is 200 Hz for now.  Display scales are in p-t-p voltages.'
     4, //' The channels are labeled starting with 0, (not 1). '
     5, / ' Questions (with non-numeric answers) can be answered'
     6, /' with first letters only'/' (UPPER or lower case).  ')
c       write(1,50)israte,iloop,inum,ichn
c       write(1,51)nopts,trglvl,itrch,idelay
c    1, bufr(3),bufr(4),bufr1(3),bufr1(4)
        return
        end
c
c -  -  -  -  -  -  -  -  -  -  -  -  -  -
c
c
        subroutine setup(icon,rcon,iall)
c
c  this subroutine is used to set up window parameters,ADC
c  parameters, etc.  Most are passed thru 2 arrays, icon and rcon
c  initially configured for storage of collection format
c
        dimension icon(32),rcon(32)
c
c
330     write(1,93)icon(10),rcon(5),icon(12)
93      format(' # points (',i4,'); Trigger:   level ('
     1 ,f8.3,'), wait (',i2,' S)? '$
```

```
              read(1,94)nopts1,trg1,idely
94            format(i0,f0.0,i0)
              if (nopts1 .gt. 0) icon(10)=nopts1
              if (trg1 .gt. 0) rcon(5)=trg1
              if (idely .gt. 0) icon(12)=idely
              write(.,933)icon(11)
933           format(2x,'Trigger channel (',i1,')? '$
              read(1,8502)itrc
8502          format(i0)
              if(itrc.gt.0) icon(11)=itrc
              icon(15) = -icon(12)*300
              if (icon(16)*2 .gt. icon(10)) icon(16)=icon(10)/2
              if (icon(10) .gt. icon(17)) write(1,8301)icon(10),icon(17)
8301          format(' Too many points! (',i5,').  Must be < ',i5)
              if (icon(10) .gt. icon(17)) goto 830
c
c now enter the channel parameters:
              write(1,120)icon(8),icon(9)
120           format(2x,'#  channels (',i2,'), starting with (',i2,')?'$
              read(1,125)inum1,ichn1
              if (inum1 .ne. 0)icon(8)=inum1
              if (inum1 .ne. 0)icon(9)=ichn1
c
125           format(2i0)
c now enter artifact parameters
c
              write(1,1255)icon(18),rcon(6),rcon(7)
1255          format(2x,'Maximum EKG points (',i4,'), minimum ICP ('
     1,        f7.2,'), tolerance (',f7.2,')? '$
              read(1,1256)mxart1,xminf1,artfc1
1256          format(i0,2f0.0)
              if (mxart1 .ne. 0) icon(18)=mxart1
              if (xminf1 .ne. 0) rcon(6)=xminf1
              if (artfc1 .ne. 0) rcon(7)=artfc1
c
c ---
              return
c
              end
c
c ------------------------- subroutine analp(icon,rcon)

c  analysis parameters dimension icon(32),rcon(32)

10            write(1,1009)icon(13)
1009          format('  Enter no. to average together,<0 to stop (',i3,')? ' $
              read(1,114)ictmx1
114           format(i0)
              if (ictmx1 .ne. 0) icon(13)=ictmx1
              if (ictmx1 .lt. 0) icon(13)=0
              write(1,10091)icon(14)
10091         format(1x,' Period for saving transform data (',i3,')? '$
              read(1,114)isave1
              if(isave1.ne.0) icon(14)=isave1
              if(isave1.lt.0) icon(14)=0
              write(1,31000)rcon(8)
31000         format(1x,'Centroid #1 delta to save waveform: (',f6.2,')? '$
              read(1,31100)dcen1
              if(dcen1.ne.0) rcon(8)=dcen1
31100         format(f0.0)
              write(1,31001)rcon(9)
31001         format(1x,'Centroid #2 delta to save waveform: (',f6.2,')? '$
              read(1,31100)dcen2
```

```
        if(dcen2.ne.0) rcon(9)=dcen2
        write(1,31002)rcon(10)
31002   format(1x,'Mean delta to save waveform: (',f6.2,')? '$
        read(1,31100)dmean1
        if(dmean1.ne.0) rcon(10)=dmean1
        return
        end
c
c  - - - - - - - - - - - - - - - - - - - - - - -
c
c
        subroutine dsplp(icon,rcon,iyca,p1,p2,p3,p4,iypos)
c
c  display parameters setup section
c
        dimension icon(32),rcon(32),iyca(6),iypos(20)
        character*30 p1,p2,p3,p4,p1a,p2a,p3a,p4a
c
c
        data mode2/2/,mode6/6/
c
c next is continuation of display parameters section
c
815     call qrmode(mode,ncol)
        if (mode .eq. 6) call qsmode(mode2)
        write(1,1101)iypos(1),iypos(2),iypos(3)
1101    format(" Enter vert posn for ICP, EKG and FFT ("
     1,i3,", ",i3," and ",i3,")? " $
        read (1,1102)iya,iyb,iyc
.102    format(3i0)
        if (iya .ne. 0) iypos(1)=iya
        if (iyb .ne. 0) iypos(2)=iyb
        if (iyc .ne. 0) iypos(3)=iyc
c
c  now set up plot positions for trend plots
c
        do 11025 kk=1,4
        write(1,11022)kk,iyca(kk)
11022   format(' Enter posn for trend # ',i1,': (',i3,')? ' $
        read(1,11023)iya
11023   format(i0)
        if (iya .ne. 0) iyca(kk)=iya
11025   continue
c
c  now set values for time bar (trend) display:
c
        write(1,11206)rcon(11),iyca(6)
11206   format (2x,'Maximum value (',f4.0,'), posn (',i3,') for time' $
        read (1,11207)clbm1,iclp1
11207   format(f0.0,i0)
        if (clbm1 .ne. 0) rcon(11)=clbm1
        if (iclp1 .ne. 0) iyca(6)=iclp1
        if (iclp1 .lt. 0) iyca(6)=0
        write(1,11208)icon(19)
11208   format(2x,'Trend plot includes each (1) or mean (2)? (now=',i1,')? '$
        read(1,11023)itrp1
        if (itrp1 .ne. 0) icon(19)=itrp1
c
        rcon(13)=rcon(15)*2
        rcon(14)=rcon(15)/2
c
        write(1,1103)icon(16),rcon(12)
1103    format(" No.points (",i4,"), maximum for FFT (",f9.1,")? " $
        read(1,1104)numa,ymaxa
1104    format(i0,f0.0)
        if (numa .ne. 0) icon(16)=numa
        if (ymaxa .gt. 0)rcon(12)=ymaxa
c
c  now which to plot
c
```

```
              write(1,1105)p1
1105    format("  Plot out : ICP (",a0,")? "  $
              read(1,1106)p1a
1106    format(a10)
              if (klen(p1a) .gt. 0) p1=p1a
              if (p1 .eq. "y") p1="Y"
c
              write(1,1109)p4
1109    format("  Plot out : ICP window (",a0,")? " $
              read(1,1106)p4a
              if (klen(p4a) .gt. 0) p4=p4a
              if (p4 .eq. "y") p4="Y"
c
              write(1,1107)p2
1107    format("  Plot out : EKG (",a0,")? " $
              read(1,1106)p2a
              if (klen(p2a) .gt. 0) p2=p2a
              if (p2 .eq. "y") p2="Y"
              write(1,1108)p3
1108    format("  Plot out : FFT (",a0,")? " $
              read(1,1106)p3a
              if (klen(p3a) .gt. 0) p3=p3a
              if (p3 .eq. "y") p3="Y"
c
              return
              end
c
c - - - - - - - - - - - - - - - - - -
c
c  Set of subroutines for program ICP
c
c *****************************************************************
c                                                                 *
c Revision History:
c 2-9-84 -AMS- extracted from ICP main program                    *
c
c *****************************************************************
c Included subroutines:
c
c
c        subroutine incnt(israte)
c        subroutine acqn(idata,inum,ichn,nopts,idebug)
c        subroutine aqtrg(itrch,trglvl,itrflg)
c        subroutine check(ichn,ians)
c        subroutine pmean(iday1,lu,icntm,centm,icount,icmx,iferr)
c        subroutine wndow (xdata,ekgdat,nleft,nopts,n1,trglvl)
c
c *****************************************************************
c
              subroutine incnt(israte)
c  subroutine initialize counter (for control of ADC)
c
              data iaddr/1808/,mode2/2/
c
c now do setup of parameters for ADC, counters etc.
c  reset DONE FF.
              x=inpt(iaddr+6)
              write(1) '  back from FF reset'
c
c
              icnt1=0
              icnt=(10000/israte)
1180    if (icnt .le. 255) goto 119
1185    icnt1=icnt1+1
              icnt=icnt-256
              goto 1180
c
119     continue
c       write(1,1191)icnt,icnt1,israte
c1191   format(2x,'icnt,icnt1,israte=',3i8,', ok? ' $
c       read(1,65)answer
```

```
c
c
c   Set data pointer to master mode register (c.f. example,pg A-26)
              call outpt(iaddr+9,23)
c   Set up master mode register for scalar control BCD division
c   enable increment, 8 bit bus, FOUT on, divide by 16, source=f1
c   comparators disabled (c.f. fig. 5, p A-23)
              call outpt(iaddr+8,0)
c   test setting this to zero
c
c             call outpt(iaddr+8,0)
c
              call outpt(iaddr+8,128)
c
c   Set data pointer to counter 3 mode register (c.f. f.4,pA-23)
c   (see example p A-28, and command summary p A-11 - bits reversed!)
              call outpt(iaddr+9,5)
c
c   No gating, rising edge of f3 (10Khz), disable special gate
c   reload from load, count repetitively, BCD count, active high TC
c   (see figure 7, page A-24 - 2 bytes transferred!)
              call outpt(iaddr+8,32)
              call outpt(iaddr+8,13)
c   Load counter with count
c   (this is accomplished through auto-sequencing to counter 3
c   2 bytes - low first - to load register - see p A-4)
              call outpt(iaddr+8,icnt)
              call outpt(iaddr+8,icnt1)
c
       return
       end
c
c   -----------------------------------------------------------------
c
       subroutine acqn(idata,inum,ichn,nopts,idebug)
c
c   acquisition subroutine
c
c   parameters passed in order are:
c
c        idata - data array (2-d)
c        inum  - number of channels to acquire
c        ichn  - 1st channel number
c        nopts - no. points to acquire per channel
c        idebug - debug flag - for special stuff to save
c
c   this assumes that hardware has been properly configured
c
       integer*1 idata(8,256)
       data iaddr/1808/,inotry/1000/,incr/128/,mode2/2/
c
       write(1,1)inum,ichn,nopts
 1     format(' Starting with: inum=',i2,', ichn=',i1,' and nopts=',i3)
c
c   test to see parameters are in correct range, compute necessary
c   pointers, etc.
c
       incr=128
       ichn1=ichn-1
       if (ichn1 .lt. 0) ichn1=255
c
c
c   set for autoincrementing of ADC channel #'s
c
c   now begin actual stuff:
c
 100   if (inum .lt. 2) goto 350
       incr=0
```

```
      now set for autoincrement (see page 50)

this jumps if only one channel is needed since autoinc not used this next is necessary to initialize autoincrementing
      according to the manual call outpt(iaddr+4,128)
            call outpt(iaddr+5,ichn1)
            call outpt(iaddr+6,0)
50       if (inpt(iaddr+4))300,250,250
00       x=inpt(iaddr+6)
      finished setup for autoincrement
            write(1) ' Finished autoinc setup ' in any case, 1 or more channels, resume here
50          call outpt(iaddr+9,112)

now set for (sequential or not) and counter armed . . .
c
            call outpt(iaddr+4,incr+4)
c  enable ext. count for ADC - either with or without autoincrementing
c
            call outpt(iaddr+5,ichn)
c  (initial channel address)
c
c           write(1,375)incr,ichn1,ichn,inum,nopts
375         format(' Now starting ADC with the following parameters:'/
     1,/,'   Autoincr flag=',i3,', dummy channel=',i3,', 1st channel=',i2
     2,/,'   Number of channels =',i2,' and number points/channel = ',i4
     3,/)
c
c
c  now begin collecting data
c
            if (idebug .eq. 1) goto 600
            do 500 i = 1, nopts
                do 500 j = 1, inum*2-1, 2
400                 if (inpt(iaddr+4)) 450,400,400
450                 idata(j,i)=inpt(iaddr+5)
                    idata(j+1,i)=inpt(iaddr+6)
500         continue
            return
c
c  now debug routine
c
600         do 650 i = 1, nopts
                do 650 j = 1, inum*2-1, 2
610                 idata(j+4,i)=inpt(iaddr+4)
                    if (idata(j+4,i)) 630,610,610
630                 idata(j,i)=inpt(iaddr+5)
                    idata(j+1,i)=inpt(iaddr+6)
650         continue
c
c   finished now
c
            return
            end
c
c  ------------------------------------------------------------
c
            subroutine aqtrg(itrch,trglvl,itrflg)
c
c   this is the triggering subroutine
c
c
c
c          itrch   - trigger channel
c          trglvl  - trigger level
c          itrflg  - flag to denote return to menu
c
            character*10 iansw,substg
            data iaddr/1808/,inotry/1000/,mode2/2/
```

```
c         write(1,1)inotry
c1        format(' no. to try for threshold? (',i4,')? ' $
c         read(1,2)inot
c2        format(i0)
c         if (inot .gt. 0) inotry=inot
c
c  reset flag
          inotry=1000
          if (itrflg .lt. 0) inotry=-itrflg
          itrflg=0
c  first loop on trigger channel until desired value is reached
          icount=0
c
10        call outpt(iaddr+4,128)
          call outpt(iaddr+5,itrch)
50        call outpt(iaddr+6,0)
c
c  this starts ADC on channel itrch (the triggering channel)
c
100       if (inpt(iaddr+4)) 150,100,100
150       ix1=inpt(iaddr+5)
          ix2=inpt(iaddr+6)
          dat=256.*ix2+ix1
          if (dat-32767.) 400,400,500
500       dat=dat-65536.
400       icount=icount+1
c         write(1,154)ix1,ix2
c154      format(2x,i5,',',i5,';'$
          if (icount .lt. inotry) goto 175
c
c  this next to get out of hopeless situations
c
          write(1,155)trglvl,inotry,dat
155       format(//' Desired level of ',f8.1,' not achieved after'
     1    ,2x,i5,' tries'//'  last level received was',f8.1,
     2    /,'  Now what? (Reset level,Main menu return,Continue) ' $
          read (1,157)iansw
          if (substg(iansw,1,1) .eq. "R") goto 156
          if (substg(iansw,1,1) .eq. "M" ) itrflg=1
          if (substg(iansw,1,1) .eq. "M" ) return
          if (substg(iansw,1,1) .eq. "r") goto 156
          if (substg(iansw,1,1) .eq. "m" ) itrflg=1
          if (substg(iansw,1,1) .eq. "m" ) return
          goto 170
c
156       write(1,160)
157       format(a10)
160       format(' Enter new threshold value: '$
          read(1,165)trglvl
          if (trglvl .ne. 0) trglvl=trglvl
165       format(f0.0)
170       icount=0
          goto 50
c
175       if (trglvl - dat) 200,50,50
c
c  leaving previous loop going to next means reached threshold
c
c NOTE! - extremely important!
c
c It cost me at least 5 hours to discover that when you
c don't use the clock to trigger, you MUST RESTART ADC
c each time you wish to take a sample.  Thus, here, jump
c to 50 instead of 100.  - BEWARE - you have been warned!
c
200       return
c
          stop
          end
c
c----------------------------------------------------
```

```
      subroutine check(ichn,ians)
c
c  this is a routine to check the value of the switch setting
c  the parameters are
c  inum - channel number to sample (0-15)
c  ians - the result:
c      1 - if 5 volts is present
c      0 - if 0 volts is present
c
      integer*1 idata(2)
      integer*2 data
      equivalence (idata,data)
      data nopts/3/,idebug/0/,imax0/2400/,iaddr/1808/
c  (imax0 is nopts*presumed value of about 3.5volts)
c
c  Acquisition of data - adapted from aqtrg
c
      iret=0
c     write(1,1000)
c1000  format(2x,'Enter channel no: '$
c     read(1,1001)ichn
c1001  format(i1)
10    call outpt(iaddr+4,128)
      call outpt(iaddr+5,ichn)
      do 900 ic=1,nopts
50    call outpt(iaddr+6,0)
c
c  this starts ADC on channel itrch (the triggering channel)
c
100   if (inpt(iaddr+4)) 150,100,100
150   idata(1)=inpt(iaddr+5)
      idata(2)=inpt(iaddr+6)
      iret=data+iret
900   continue
c     write(1,154)idata(1),idata(2),data,iret
c154   format(2x,'ix1,ix2: ',i5,i5,' data:',i5,' iret:',i5)
c
c
      ians=0
      if (iret .gt. imax0)ians=1
      return
      end
c
c ---------------------
c
      subroutine pmean(iday1,lu,icntm,centm,icount,icmx,iferr)
c
c  this prints out mean values whenever change is made
c
      dimension centm(6)
c
c
      if ((icmx .eq. 0) .or. (icntm .eq. 0) )return
c
c
      centm(1)=centm(1)/icntm
      centm(3)=centm(3)/icntm
      centm(2)=centm(2)/icntm
      centm(4)=centm(4)/icntm
2023  call gtime(ihrs,mins,isec,icsec)
      tmicp=centm(5)/icntm
      if (lu .ne. 0) write(lu,2026)
     1  centm(1),centm(3)
     2,   tmicp,ihrs,mins,iday1,icntm
2026  format(2x,'M:C1=',f5.2,', C2=',f5.1
     1,   ', ICP = ',f4.0,' mm at ',i2,':',i2,', day ',i2,',N=',i2)
20251 write(6,endfile=10000,errexit=10010)ihrs,mins,centm(1),centm(2)
     1,centm(3),centm(4),tmicp,iday1
      icntm=0
```

```
              centm(1)=0
              centm(3)=0
              centm(2)=0
              centm(4)=0
              icount=0
              centm(5)=0
              iferr=0
              goto 9999
10000         write(1,10001)
10001         format(1x,'Centroid end of file error!')
              iferr=1
              goto 9999
10010         write(1,10011)
10011         format(1x,'Centroid file error!')
              iferr=2
9999          return
              end
c
c    ------------------------------------------------
c
              subroutine wndow (xdata,ekgdat,nleft,nopts,n1,trglvl)
c
c   this subroutine is used to window the icp data according to the
c   EKG data.  It assumes that the trace is triggered by the QRS
c   complex and that the initial value of the EKG array is an
c   appropriate threshold level.  The parameters passed are:
c
c       xdata - icp data
c       ekgdat - EKG array
c       nleft  - returned index marking end of the first cycle
c                nleft<0 indicates that windowing was not
c       nopts - no. points collected in the original data
c       n1 - sample rate per channel - used to define start. point
c       trglvl - the EKG trigger level
c
              dimension ekgdat(256),xdata(256)
c
              nstart=3*n1/10
c   this is supposed to be 300 ms after the 1st QRS complex
              do 100 i=nstart,nopts
              if (ekgdat(i) .lt. trglvl) goto 100
              nleft=i
              goto 200
100           continue
              nleft=-1
              return
c
200           if (nleft.lt.10) nleft=1
              if (nleft.ge.10) nleft=nleft-9
c
              istart=n1/10
c   this is the starting offset for icp - to move to beginning
c   of ICP wave assuming a fixed 100 mS delay from QRS pulse to
c   ICP pulse beginning as seen in the ventricular pressure mon.
c
              n500=n1/2
              if (nleft+n500 .gt. nopts) n500=nopts-nleft
c   n500 is the number of points equal to 500 mS
c
              if (xdata(nleft) .gt. xdata(istart)) goto 400
c
              do 300 i=nleft,nleft+n500
              if (xdata(i) .lt. xdata(istart)) goto 300
              nleft=i
              goto 500
300           continue
              nleft=-2
              return
c
400           do 450 i=nleft,nleft+n500
              if (xdata(i) .gt. xdata(istart)) goto 450
```

```
            nleft=i
            goto 500
450     continue
        nleft=-2
        return
c
500     do 600 i=nleft+1,nopts
600     xdata(i)=xdata(istart)
        do 700 i=1,istart-1
700     xdata(i)=xdata(istart)
        return
        end
        subroutine centr(spec,bufr,cent,pspec,pfreq)
c
c
c    this subroutine TAKES AN ARRAY AND FINDS THE CENTROID OF ITS DATA
c    THE PROGRAM ASSUMES THAT THE NUMBER OF POINTS IS LESS THAN OR EQUAL
c    TO 2048, AND THAT THE ARRAY VALUES ARE EVENLY SPACED DATA POINTS.
c    THE USER MUST INPUT THE FIRST AND LAST FREQUENCIES (IN HZ) TO Be
c    INCLUDED IN THE CENTROID CALCULATION, AS WELL AS THE NAME OF THE
c    DATA SET CONTAINING THE DATA.  THE ARRAY WILL BE ZEROED OUT, SO
c    SETS OF DATA LESS THAN 2048 LONG CAN BE USED.
c
c    PROGRAM ALGORITHM DEVELOPED ON 8/29/80 BY KEVIN R. LIND,
c    P.O. BOX 2671, HOUSTON, TX 77001.  INITIAL CODING ON 8/30/80
c
c    MODIFICATIONS:  (GIVE BRIEF DESCRIPTION, NAME, AND DATE)
c
c    23 October 1983 - changed parameter array to real, changed check
c                      on upper limit to freq/2 (AMS).
c    1 September, 1983 -AMS- converted to subroutine for IBM PC-XT
c    5  December 1982 - Added compution of area and peak powers
c    19 December 1980 - modified for easier entry of data, requires *L3
c                       and to simplify output format
c
c    The following parameters are passed to subroutine:
c
c         spec - the power spectral array (real - max 256)
c         bufr  - integer array of parameters as follows:
c              bufr(1) - no. of points in array
c              bufr(2) - sample period in uS for this channel
c              bufr(3) - beginning of centroid window
c              bufr(4) - end of sample window (Hz)
c              bufr(5) - flag for printing - 1=yes, 2=no
c         cent - the centroid value (real) returned to calling prog
c         pspec - the peak power in the spectrum window
c         pfreq - the peak frequency REAL SPEC(256),PWR,CENT,CONV,FREQ,DFREQ,FFREQ,LFREQ,lfrq,bufr(5)
        INTEGER FBIN,LBIN,I,LU,ANS,NUM,RATE,MULT,MRATE
c
1       SPEC(1)=0.0
c
c SET TOTAL POWER AND CENTROID TO ZERO INITIALLY
        PWR=0.0
        CENT=0.0
c INITIALIZE FREQUENCY INFORMATION
        NUM=bufr(1)

MRATE=bufr(2)
c FIND STEP IN FREQUENCY BETWEEN ARRAY POSITIONS
        FREQ=1.0/FLOAT(MRATE) * 1.0E6
        DFREQ=FREQ/NUM
c SET MAXIMUM FREQUENCY RANGE FOR 256 POINT MAXIMUM
        IF(NUM .GT. 256) FREQ=DFREQ*256.0
c INDICATE FREQUENCY RANGE AND STEP
039     FFREQ=bufr(3)
        LFREQ=bufr(4)
        IF (bufr(5) .ne. 1.) GOTO 1041
        call vcurxy(0,22)
``` this repositions cursor to next to bottom line of screen
```
      WRITE(1,1035)FREQ,DFREQ
1035  format(/,/' Frequency range - ',f5.1,'Hz, step size - ',f5.1)
C INPUT FIRST AND LAST FREQUENCIES DESIRED
C
      WRITE(1,1040)FFREQ,LFREQ
1040  FORMAT(' Enter FIRST and Last frequencies desired (',2f5.1,') '$
      READ(1,5060)ffrq,LFRq
5060     format(f0.0,f0.0)
         if (ffrq .gt. 0) ffreq = ffrq
         if (lfrq .gt. ffreq) lfreq = lfrq
         bufr(3)=ffreq
         bufr(4)=lfreq
C TRUNCATE IF NECESSARY
1041  if (lfreq .gt. freq/2) lfreq=freq/2
c
C CALCULATE CORRESPONDING ARRAY POSITIONS
      FBIN=INT(FFREQ/DFREQ)+1
      LBIN=INT(LFREQ/DFREQ)+1
c     write(4,10420)fbin,lbin,dfreq
c10420 format(' Fbin=',i5,' Lbin=',i5,' Dfreq=',f8.2)
      IF(FBIN .LE. NUM) GO TO 30
         WRITE(1,1055)
1055     FORMAT(' first frequency too high')
         GO TO 9999
30    CONTINUE
C
C CALCULATE CENTROID
C
C ACCUMULATE TOTAL POWER AND SECOND MOMENT
      PSPEC=0.
      PFREQ=0.
      DO 2010 I=FBIN,LBIN,1
         PWR=PWR+SPEC(I)
         CONV=I*DFREQ
         CENT=CENT+CONV*SPEC(I)
      IF(SPEC(I).LE.PSPEC)GO TO 2010
      PSPEC=SPEC(I)
      PFREQ=CONV
2010  CONTINUE
C CENTROID IS SECOND MOMENT DIVIDED BY TOTAL POWER
      CENT=CENT/PWR
C WRITE OUT VALUE ON DEVICE DESIRED
      LU1=1
      if (bufr(5) .ne. 1.) return
      WRITE(LU1,1080)FFREQ,LFREQ,CENT
1080     format(/,' Centroid over',f4.1,' to ',f4.1,' is ',f5.2,' Hz')
      WRITE(1,5010)pwr
      write(1,5020)pspec,pfreq
5010     format(16x,'Total power (area) = ',f8.0)
5020     format(16x,'Peak power is =',F8.2,15x,' at: ',f4.1,' Hz.')
      if (pspec .eq. 0) pspec = .001
      pwrat=pwr/pspec
      WRITE(1,5030)pwrat
5030  format(16X,'Spectral spread (tot. power/peak power) = ', f5.2)
      write(1,5040)
5040     format(' ')
c
c end of calculations
c
9999     return
         end
         dimension icon(32),rcon(32)
         character*30 answer,name,date,coment,substg,answ1,ans,p1,p2,p3
     1   , p1a,p2a,p3a,ans2,ans21,p4,p4a,wind,fname1,fname2,fname3
     2,  name2,name1,ncnt,fname,fname4,next
         character*70 commnt
         character*512 data
         character*2 start,begin
         character*20 bogus,real
         integer*1 idata,esc,imask
```

```
      real lcent1,lcent2,lmean
      data bogus/'            '/,real/'00:00   '/
      data fname1/""/,fname2/""/,fname3/""/,esc/27/,fname4/""/
      data kolor/7/,mode2/2/,mode6/6/,ix/1/,iy/100/,ymax/3000./
      data nopts/256/,npts/256/,next/"C"/
      dimension idata(512),dat1(3,1024),itime(512),xdata(256)
      equivalence (iyear,icon(1)),(month,icon(2))
     1,(iday,icon(3)),(ihrs,icon(4)),(mins,icon(5)),(israte,icon(6))
     2,(ilocp,icon(7)),(inum,icon(8)),(ichn,icon(9))
     3,(nopts,icon(10)),(itrch,icon(11)),(idelay,icon(12))
     4,(icmx,icon(13)),(isave,icon(14)),(cent11,rcon(1))
     5,(centh1,rcon(2)),(centl2,rcon(3)),(centh2,rcon(4))
     6, (trglvl,rcon(5))
c
c
c
c - - - - - - - -
c initialize printout
c
      write(1,10)
10    format(1x,'Enter file name: '$
      read(1,11000)fname
11000 format(a0)
c
c File open section
c
      call addstg(fname1,fname,".asc")
      if (iolook(0,fname1)) goto 121
      goto 12
c
c  file exists, open file
c
121   call addstg(fname2,fname, .cen")
      call addstg(fname3,fname,".wav")
      call addstg(fname4,fname,".com")
      if (ioread(5,0,0,fname1)) goto 200
      if (ioread(6,0,0,fname2)) goto 200
      if (ioread(7,0,0,fname3)) goto 200
      if (ioread(8,0,0,fname4)) goto 200
      read(5,endfile=900,errexit=950)name2,name1
      read(5,endfile=900,errexit=950)(icon(i),i=1,32)
      read(5,endfile=900,errexit=950)(rcon(i),i=1,32)
      write(1,1001)name1,name2
1001  format(1x,"Name: ",a0," ",a0)
      write(1,2010)fname
2010  format(/1x,'Waveform index for file: ',a0)
      write(1,2020)month,iday,iyear
2020  format(/1x,'Date: ',i2,'/',i2,'/',i4/)
2100  read(7,endfile=500,errexit=950)ihrs,mins
      read(7,endfile=500,errexit=950)(xdata(i),i=1,nopts)
      icnt=icnt+1
      write(1,2000)icnt,ihrs,mins
2000  format(10x,'waveform #',i3,' time: ',i2,':',i2)
      goto 2100
500   iwave=1
1800  write(1,2040)iwave
2040  format(/1x,'Display waveform # (',i3,') ?'$
      read(1,2050)iwave1
2050  format(i0)
      if(iwave1.ne.0) iwave=iwave1
c
c  Index in to waveform
c
      if (ioclos(7)) goto 9990
      if(ioread(7,0,0,fname3)) goto 200
      do 3000 ind=1,iwave
      read(7,endfile=600,errexit=950)ihrs,mins
3000  read(7,endfile=600,errexit=950)(xdata(i),i=1,nopts)
      iwave=iwave+1
      dmin=0.
      dmax=0.
```

```
              xsum=0.
              do 2900 iz=1,nopts
              xsum=xdata(iz)+xsum
              if(xdata(iz).lt.dmin)dmin=xdata(iz)
2900          if(xdata(iz).gt.dmax)dmax=xdata(iz)
              xmean=xsum/nopts
              do 2990 iz=1,nopts
2990          xdata(iz)=xdata(iz)-xmean
              drange=dmax-dmin
              ymax=drange*2
2500          call qsmode(mode6)
              call pline(ix,iy,xdata,kolor,npts,ymax,npts)
              write(1,2060)ihrs,mins
2060          format(1x,'time: ',i2,':',i2)
              read(1,2050)igarb
              call qsmode(mode2)
              write(1,2070)next
2070          format(1x,'Continue, Vert., Horz. or Quit: (',a0,') ?'$
              read(1,2080)answer
2080          format(a0)
              if(klen(answer).ne.0) next=answer
              if (substg(next,1,1).eq."Q") goto 9000
              if (substg(next,1,1).eq."q") goto 9000
              if (substg(next,1,1).eq."V") goto 1500
              if (substg(next,1,1).eq."v") goto 1500
              if (substg(next,1,1).eq."H") goto 1700
              if (substg(next,1,1).eq."h") goto 1700
              goto 1800
1500          write(1,1510)ymax
1510          format(1x,'Enter scale: (',f10.2,') ?'$
              read(1,1520)ymax1
1520          format(f0.0)
              if(ymax1.ne.0)ymax=ymax1
              ymax1=0
              goto 2500
1700          write(1,1750)npts
1750          format(1x,'Number of points: (',i3,') ?'$
              read(1,1751)npts
1751          format(i0)
              goto 2500
600           write(1,650)
650           format(1x,'End of file')
              goto 1800
9000          stop
900           write(1,901)
901           format(1x,'End of file condition')
              stop
951           format(1x,'error in file read')
              stop
12            write(1,122)
122           format(1x,'file not found')
              stop
200           write(1,201)
201           format(1x,'file open error!')
              stop
9990          write(1,9995)
9995          format(1x,'File close error!')
              stop
              end
              dimension icon(32),rcon(32)
              character*30 answer,name,date,coment,substg,answ1,ans,p1,p2,p3
     1        ,p1a,p2a,p3a,ans2,ans21,p4,p4a,wind,fname1,fname2,fname3
     2,       name2,name1,ncnt,fname,fname4
              character*70 commnt
              character*512 data
              character*2 start,begin
              character*20 bogus,real
              integer*1 idata,esc,imask
              real lcent1,lcent2,lmean
              data bogus/'            '/,real/'00:00     '/
```

```
      data fname1/""/,fname2/""/,fname3/""/,esc/27/,fname4/""/
      dimension idata(512),dat1(3,2048),itime(4096)
      equivalence (iyear,icon(1)),(month,icon(2))
     1,(iday,icon(3)),(ihrs,icon(4)),(mins,icon(5)),(israte,icon(6))
     2,(iloop,icon(7)),(inum,icon(8)),(ichn,icon(9))
     3,(nopts,icon(10)),(itrch,icon(11)),(idelay,icon(12))
     4,(icmx,icon(13)),(isave,icon(14)),(cent11,rcon(1))
     5,(centh1,rcon(2)),(cent12,rcon(3)),(centh2,rcon(4))
     6,(trglvl,rcon(5))
c
c
c
c - - - - - - - - -
c initialize printout
c
      write(1,10)
10    format(1x,'Enter file name: '$
      read(1,11000)fname
11000 format(a0)
c
c File open section
c
      call addstg(fname1,fname,".asc")
      if (iolook(0,fname1)) goto 121
      goto 12
c
c file exists, open file
c
121   call addstg(fname2,fname,".cen")
      call addstg(fname3,fname,".wav")
      call addstg(fname4,fname,".com")
      if (ioread(5,0,0,fname1)) goto 200
      if (ioread(6,0,0,fname2)) goto 200
      if (ioread(7,0,0,fname3)) goto 200
      if (ioread(8,0,0,fname4)) goto 200
      read(5,endfile=900,errexit=950)name2,name1
      read(5,endfile=900,errexit=950)(icon(i),i=1,32)
      read(5,endfile=900,errexit=950)(rcon(i),i=1,32)
      write(1,1001)name1,name2
1001  format(1x,"Name: ",a0," ",a0)
      write(1,1010)
      read(1,1011)zcent1,range1
      write(1,1012)
      read(1,1011)zcent2,range2
      write(1,1014)
      read(1,1011)zmean,rangem
1010  format(1x,'Enter centroid #1 center frequency, +- range: '$
1012  format(1x,'Enter centroid #2 center frequency, +- range: '$
1014  format(1x,'Enter mean pressure, +- range: '$
1011  format(f0.0,f0.0)
      lcent1=zcent1-range1
      hcent1=zcent1+range1
      lcent2=zcent2-range2
      hcent2=zcent2+range2
      lmean=zmean-rangem
      hmean=zmean+rangem
      call putchr(start,1,esc)
      call addstg(start,"0")
      write(4,1035)
1035  format('1',//,1x,'Trend plot of ICP data',/)
      write(4,1040)start
1040  format(1x,a0)
      call setlen(start,0)
      write(4,1020)fname
1020  format(1x,'File name: ',a0)
      write(4,1021)name1,name2
      write(4,1022)month,iday,iyear
1022  format(1x,'Date: ',i2,'/',i2,'/',i4/)
1021  format(1x,/,1x,'Patient name: ',a0,' , ',a0/)
150   read(8,endfile=3000,errexit=950)ihrs,mins,commnt
      if(klen(commnt).eq.0)goto 160
      write(4,1030)ihrs,mins,commnt
```

```
1030       format(1x,'Time: ',i2,':',i2,'   comment:    ',a0)
           call setlen(commnt,0)
160        goto 150
c
c
3000       nloop=1
c
100        read(6,endfile=2000,errexit=950)ihrs,mins,cent1,peak1
      1    ,cent2,peak2,tmicp,iday
           dat1(1,nloop)=cent1
           dat1(2,nloop)=cent2
           dat1(3,nloop)=tmicp
           itime((nloop-1)*2+1)=ihrs
           itime((nloop-1)*2+2)=mins
c          write(1,1003)ihrs,mins,iday
c1003       format(1x,'Time: ',i2,':',i2,', day: ',i2)
c          write(1,1004)cent1,peak1,cent2,peak2,tmicp
c1004       format(1x,5(f10.2))
           nloop=nloop+1
           if (nloop .gt. 1024) goto 999
           goto 100
c
c    Trend plot routine
c
c    Uses 100 points across
c
2000       write(4,1050)
1050       format(///,1x)
           write(4,1060)
1060       format(2x,'time',8x,'centroid 1',15x,'centroid 2',15x,'mean icp'/)
           write(4,1070)lcent1,zcent1,hcent1,lcent2,zcent2,hcent2,lmean,zmean,hmean
1070       format(6x,3(3(f6.2,2x),2x))
           ibump=3
           call putchr(start,1,esc)
           call addstg(start,"1")
           imask=!C0!
           call putchr(data,1,esc)
           call addstg(data,"K")
           call putchr(data,3,144)
           call putchr(data,4,1)
           write(4,15)start
15         format(1x,a0)
           do 55 iloop=1,512
55         idata(iloop)=0
           do 105 i=1,nloop
           do 225 i1=1,3
           if(i1.eq.1)range=range1
           if(i1.eq.1)zero=zcent1
           if(i1.eq.2)range=range2
           if(i1.eq.2)zero=zcent2
           if(i1.eq.3)range=rangem
           if(i1.eq.3)zero=zmean
           indx=50+150*(i1-1)+(50/range)*(dat1(i1,i)-zero)
           if(i1.ne.1)goto230
           if(indx.gt.100)indx=100
           if(indx.lt.1)indx=1
230        if(i1.ne.2)goto240
           if(indx.gt.250)indx=250
           if(indx.lt.150)indx=150
240        if(i1.ne.3)goto250
           if(indx.gt.400)indx=400
           if(indx.lt.300)indx=300
250        idata(indx)=idata(indx).or.imask
225        idata(indx+1)=idata(indx+1).or.imask
           if (imask.eq.1) goto 205
           imask=ishift(imask,-1)
           goto 105
205        do 305 iloop=1,400
305        call putchr(data,iloop+4,idata(iloop))
           ibump=ibump+1
           if(ibump.eq.4) goto 605
           write(4,1005)bogus,data
```

```
1005      format(1x,a10,a0)
          goto 505
505       write(4,1006)itime((i-1)*2+1),itime((i-1)*2+2),data
1006      format(1x,i2,':',i2,'      ',a0)
          ibump=0
305       do 405 iloop=1,512
405       idata(iloop)=0
          imask=!C0!
          do 7225 i1=1,3
          if(i1.eq.1)range=range1
          if(i1.eq.1)zero=zcent1
          if(i1.eq.2)range=range2
          if(i1.eq.2)zero=zcent2
          if(i1.eq.3)range=rangem
          if(i1.eq.3)zero=zmean
          indx=50+150*(i1-1)+(50/range)*(dat1(i1,i)-zero)
          if(i1.ne.1)goto7230
          if(indx.gt.100)indx=100
          if(indx.lt.1)indx=1
7230      if(i1.ne.2)goto7240
          if(indx.gt.250)indx=250
          if(indx.lt.150)indx=150
7240      if(i1.ne.3)goto7250
          if(indx.gt.400)indx=400
          if(indx.lt.300)indx=300
7250      idata(indx)=!80!
7225      idata(indx+1)=!80!
405       continue
          stop
900       write(1,901)
901       format(1x,'End of file condition')
          stop
950       write(1,951)
951       format(1x,'error in file read')
          stop
12        write(1,122)
122       format(1x,'file not found')
          stop
999       write(1,9991)
9991      format(1x,'too many points! I quit reading!')
          goto 2000
200       write(1,201)
201       format(1x,'file open error!')
          stop
          end
          dimension icon(32),rcon(32)
          character*30 answer,name,date,coment,substg,answ1,ans,p1,p2,p3
     1  , p1a,p2a,p3a,ans2,ans21,p4,p4a,wind,fname1,fname2,fname3
     2, name2,name1,ncnt,fname,fname4
          character*70 commnt
          character*512 data
          character*2 start,begin
          character*20 bogus,real
          integer*1 idata,esc,imask
          real lcent1,lcent2,lmean
          data bogus/'           '/,real/'00:00      '/
          data fname1/""/,fname2/""/,fname3/""/,esc/27/,fname4/""/
          dimension idata(512),dat1(3,2048),itime(4096)
          equivalence (iyear,icon(1)),(month,icon(2))
     1,(iday,icon(3)),(ihrs,icon(4)),(mins,icon(5)),(israte,icon(6))
     2,(iloop,icon(7)),(inum,icon(8)),(ichn,icon(9))
     3,(nopts,icon(10)),(itrch,icon(11)),(idelay,icon(12))
     4,(icmx,icon(13)),(issve,icon(14)),(cent11,rcon(1))
     5,(centh1,rcon(2)),(cent12,rcon(3)),(centh2,rcon(4))
     6, (trglvl,rcon(5))
c
c
c
c - - - - - - - - - -
c initialize printout
c
```

```
            write(1,10)
10          format(1x,'Enter file name: '$
            read(1,11000)fname
11000       format(a0)
c
c File open section
c
            call addstg(fname1,fname,".asc")
            if (iolook(0,fname1)) goto 121
            goto 12
c
c  file exists, open file
c
121         call addstg(fname2,fname,".cen")
            call addstg(fname3,fname,".wav")
            call addstg(fname4,fname,".com")
            if (ioread(5,0,0,fname1)) goto 200
            if (ioread(6,0,0,fname2)) goto 200
            if (ioread(7,0,0,fname3)) goto 200
            if (ioread(8,0,0,fname4)) goto 200
            read(5,endfile=900,errexit=950)name2,name1
            read(5,endfile=900,errexit=950)(icon(i),i=1,32)
            read(5,endfile=900,errexit=950)(rcon(i),i=1,32)
            write(1,1001)name1,name2
1001        format(1x,"Name: ",a0," ",a0)
            write(1,1010)
            read(1,1011)zcent1,range1
            write(1,1012)
            read(1,1011)zcent2,range2
            write(1,1014)
            read(1,1011)zmean,rangem
1010        format(1x,'Enter centroid #1 center frequency, +- range: '$
1012        format(1x,'Enter centroid #2 center frequency, +- range: '$
1014        format(1x,'Enter mean pressure, +- range: '$
1011        format(f0.0,f0.0)
            lcent1=zcent1-range1
            hcent1=zcent1+range1
            lcent2=zcent2-range2
            hcent2=zcent2+range2
            lmean=zmean-rangem
            hmean=zmean+rangem
            call putchr(start,1,esc)
            call addstg(start,"0")
            write(4,1035)
1035        format('1',//,1x,'Trend plot of ICP data',/)
            write(4,1040)start
1040        format(1x,a0)
            call setlen(start,0)
            write(4,1020)fname
1020        format(1x,'File name: ',a0)
            write(4,1021)name1,name2
            write(4,1022)month,iday,iyear
1022        format(1x,'Date: ',i2,'/',i2,'/',i4/)
1021        format(1x,/,1x,'Patient name: ',a0,' , ',a0/)
150         read(8,endfile=3000,errexit=950)ihrs,mins,commnt
            if(klen(commnt).eq.0)goto 160
            write(4,1030)ihrs,mins,commnt
1030        format(1x,'Time: ',i2,':',i2,'  comment: ',a0)
            call setlen(commnt,0)
160         goto 150
c
3000        nloop=1
c
100         read(6,endfile=2000,errexit=950)ihrs,mins,cent1,peak1
     1      ,cent2,peak2,tmicp,iday
            dat1(1,nloop)=cent1
            dat1(2,nloop)=cent2
            dat1(3,nloop)=tmicp
            itime((nloop-1)*2+1)=ihrs
            itime((nloop-1)*2+2)=mins
c           write(1,1003)ihrs,mins,iday
```

```
c1003       format(1x,'Time: ',i2,':',i2,', day: ',i2)
c           write(1,1004)cent1,peak1,cent2,peak2,tmicp
c1004       format(1x,5(f10.2))
            nloop=nloop+1
            if (nloop .gt. 1024) goto 999
            goto 100
c
c   Trend plot routine
c
c   Uses 100 points across
c
2000        write(4,1050)
1050        format(///,1x)
            write(4,1060)
1060        format(2x,'time',8x,'centroid 1',15x,'centroid 2',15x,'mean icp'/)
            write(4,1070)lcent1,zcent1,hcent1,lcent2,zcent2,hcent2,lmean,zmean,hmea
1070        format(6x,3(3(f6.2,2x),2x))
            ibump=3
            call putchr(start,1,esc)
            call addstg(start,"1")
            imask=!CO!
            call putchr(data,1,esc)
            call addstg(data,"K")
            call putchr(data,3,144)
            call putchr(data,4,1)
            write(4,15)start
15          format(1x,a0)
            do 55 iloop=1,512
55          idata(iloop)=0
            do 105 i=1,nloop
            do 225 i1=1,3
            if(i1.eq.1)range=range1
            if(i1.eq.1)zero=zcent1
            if(i1.eq.2)range=range2
            if(i1.eq.2)zero=zcent2
            if(i1.eq.3)range=rangem
            if(i1.eq.3)zero=zmean
            indx=50+150*(i1-1)+(50/range)*(dat1(i1,i)-zero)
            if(i1.ne.1)goto230
            if(indx.gt.100)indx=100
            if(indx.lt.1)indx=1
230         if(i1.ne.2)goto240
            if(indx.gt.250)indx=250
            if(indx.lt.150)indx=150
240         if(i1.ne.3)goto250
            if(indx.gt.400)indx=400
            if(indx.lt.300)indx=300
250         idata(indx)=idata(indx).or.imask
225         idata(indx+1)=idata(indx+1).or.imask
            if (imask.eq.1) goto 205
            imask=ishift(imask,-1)
            goto 105
205         do 305 iloop=1,400
305         call putchr(data,iloop+4,idata(iloop))
            ibump=ibump+1
            if(ibump.eq.4) goto 605
            write(4,1005)bogus,data
1005        format(1x,a10,a0)
            goto 505
605         write(4,1006)itime((i-1)*2+1),itime((i-1)*2+2),data
1006        format(1x,i2,':',i2,'        ',a0)
            ibump=0
505         do 405 iloop=1,512
405         idata(iloop)=0
            imask=!CO!
            do 7225 i1=1,3
            if(i1.eq.1)range=range1
            if(i1.eq.1)zero=zcent1
            if(i1.eq.2)range=range2
            if(i1.eq.2)zero=zcent2
            if(i1.eq.3)range=rangem
```

```
              if(i1.eq.3)zero=zmean
              indx=50+150*(i1-1)+(50/range)*(dat1(i1,i)-zero)
              if(i1.ne.1)goto7230
              if(indx.gt.100)indx=100
              if(indx.lt.1)indx=1
7230          if(i1.ne.2)goto7240
              if(indx.gt.250)indx=250
              if(indx.lt.150)indx=150
7240          if(i1.ne.3)goto7250
              if(indx.gt.400)indx=400
              if(indx.lt.300)indx=300
7250          idata(indx)=!80!
7225          idata(indx+1)=!80!
105           continue
              stop
900           write(1,901)
901           format(1x,'End of file condition')
              stop
950           write(1,951)
951           format(1x,'error in file read')
              stop
12            write(1,122)
122           format(1x,'file not found')
              stop
999           write(1,9991)
9991          format(1x,'too many points! I quit reading!')
              goto 2000
200           write(1,201)
201           format(1x,'file open error!')
              stop
              end
              subroutine pfill(ix,iy,array,kolor,num,ymax,nplot)
c
c   this routine is to plot the array of points on the screen
c   The points in the array passed are plotted with a line extending
c   from the baseline to the data value.
c
c   the parameters are:
c
c   ix      -       initial column for plot
c   iy      -       initial row for plot
c   array   -       data array containing values to plot
c   kolor   -       color of line to plot
c   num     -       number of points to allow space to plot in X dir.
c   ymax    -       peak-to-peak value of y variable
c   nplot   -       number of points to actually plot
c
c
c   the array sclmod is used to point to the correct size according
c   to which mode you are in currently
c
              dimension array(200),modscl(7)
              data modscl/40,40,80,80,320,320,640/
c
c   initialize plot constants:
              call qrmode(mode,ncol)
c
c   debug print statements
c
c             write(1,900)mode,ncol
c900          format("  mode is",i2,", and no columns=",i2)
              if (nplot .gt. num) num=nplot
              xinc = 1.*modscl(mode+1)/num
              scale = 199./ymax
              jcol1=ix
              jrow1=iy
              if (jrow1 .gt. 199) jrow1=199
              if (jrow1 .lt. 0) jrow1=0
c
c   debug print statements
c
```

```
c       write(1,910)ix,iy,xinc,scale
c910    format("  ix,iy=",2i4,",xinc=",f6.3,", scale=",f6.3)
c       write(1,920)kolor
c920    format("  plotting color is",i3)
c       write(1)   "  begin plotting now!"
c
c
        do 100 i=1,nplot
        jcol2=jcol1
        jrow2=int(scale*array(i))+iy
        if (jrow2 .gt. 199) jrow2=199
        if (jrow2 .lt. 0) jrow2=0
        call qline (jcol1,jrow1,jcol2,jrow2,kolor)
100     jcol1=ix+xinc*i
        return
        end
        subroutine pline(ix,iy,array,kolor,num,ymax,nplot)
c
c   this routine is to plot the array of points on the screen
c
c   the parameters are:
c
c   ix      -    initial column for plot
c   iy      -    initial row for plot
c   array   -    data array containing values to plot
c   kolor   -    color of line to plot
c   num     -    number of points to allow space to plot in X dir.
c   ymax    -    peak-to-peak value of y variable
c   nplot   -    number of points to actually plot
c
c
c
c   the array sclmod is used to point to the correct size according
c   to which mode you are in currently
c
        dimension array(200),modscl(7)
        data modscl/40,40,80,80,320,320,640/
c
c   initialize plot constants:
        call qrmode(mode,ncol)
c
c   debug print statements
c
        write(1,900)mode,ncol
c900    format("  mode is",i2,", and no columns=",i2)
        if (nplot .gt. num) num=nplot
        xinc = 1.*modscl(mode+1)/num
        scale = 199./ymax
        jcol1=ix
        jrow1=iy+int(scale*array(1))
        if (jrow1 .gt. 199) jrow1=199
        if (jrow1 .lt. 0) jrow1=0
c
c   debug print statements
c
        write(1,910)ix,iy,xinc,scale
c910    format("  ix,iy=",2i4,",xinc=",f6.3,", scale=",f6.3)
c       write(1,920)kolor
c920    format("  plotting color is",i3)
c       write(1)   "  begin plotting now!"
c
c
        do 100 i=1,nplot-1
        jcol2=ix+xinc*i
        jrow2=int(scale*array(i+1))+iy
        if (jrow2 .gt. 199) jrow2=199
        if (jrow2 .lt. 0) jrow2=0
        call qline (jcol1,jrow1,jcol2,jrow2,kolor)
        jcol1=jcol2
00      jrow1=jrow2
        return
        end
```

What is claimed is:

1. An apparatus for analyzing changes in the waveform generated by variations of pressure within an organ of a living body comprising:
   pressure sensing means adapted to be placed within an organ of a living body for measuring the pressure within said organ of said body;
   pressure transducer means connected to said pressure sensing means for converting the measured values of pressure to an analog electrical signal waveform indicative of the waveform generated by the variations of pressure over time within said organ of said body;
   analog to digital converter means electrically connected to said pressure transducer means for converting said analog electrical signal waveform into digital electrical signals indicative of said pressure waveform, for digital computer analysis;
   computing means electrically connected to said analog to digital converter means for mathematically computing a distribution of the amplitude of said pressure waveform versus the frequency components of said pressure waveform and analyzing said frequency distribution to indicate physiological conditions within said organ of said body;
   electrical transducing means, adapted to be connected to the living body to obtain parameters of the cardiac cycle and the respiratory cycle to be correlated with said analog electrical signal waveform from said pressure transducer means to determine the optimal time during said cardiac and respiratory cycles for analysis of said frequency distribution to achieve the most accurate physiological interpretation of said frequency distribution, said electrical transducing means being connected to said analog to digital converter means; and
   output means electrically connected to said computing means for displaying the results of said mathematical analysis.

2. An apparatus for analyzing changes in the waveform generated by variations of intracranial pressure within the brain of a living body comprising:
   pressure sensing means adapted to be placed within the brain of a living body for measuring the intracranial pressure within the brain of said body;
   pressure transducer means connected to said pressure sensing means for converting the measured values of intracranial pressure to an analog electrical signal waveform indicative of the waveform generated by the variations of intracranial pressure over time within the brain of said body;
   analog to digital converter means electrically connected to said pressure transducer means for converting said analog electrical signal waveform into digital electrical signals indicative of said intracranial pressure waveform for digital computer analysis;
   computing means electrically connected to said analog to digital converter means for mathematically, computing a distribution of the amplitude of said intracranial pressure waveform versus the frequency components of said intracranial pressure waveform and analyzing said frequency distribution to indicate the cerebral compliance and the cerebral blood flow within the brain of said body;
   electrical transducing means adapted to be connected to the living body to obtain parameters of the to the living body to obtain parameters of the cardiac cycle and the respiratory cycle to be correlated with said analog electrical signal waveform from said pressure transducer means to determine the optimal time during said cardiac and respiratory cycles for analysis of said frequency distribution to achieve the most accurate physiological interpretation of aid frequency distribution, said electrical transducing means being connected to said analog to digital converter means; and
   output means electrically connected to said computing means for displaying the results of said mathematical analysis.

3. An apparatus as claimed in claim 2, wherein
   said electrical transducing means includes electrocardiograph means adapted to be connected to said living body for measuring the analog electrical signals of the heart of said living body to delineate the cardiac cycle; and
   at least one signal line electrically connecting said electrocardiograph means and said analog to digital converter means, transmitting said analog electrical signals from said electrocardiograph means to said analog to digital converter means for conversion into digital electrical signals and subsequently to said computing means for correlation and gating of the digital electrical signals indicative of the intracranial pressure waveform.

4. An apparatus as claimed in claim 3 together with
   respirator gating means connected within at least one signal line electrically connecting said electrocardiograph means and said analog to digital converter means for regulating the transmission of the electrical signal from said electrocardiograph means on said signal line to said analog to digital converter means;
   a respirator pressure switch connected to a respirator adapted to be connected to said living body, said switch determining when said living body is exhaling and when said living body is inhaling, said respirator pressure switch electrically connected to said respirator gating means to provide said respirator gating means with information concerning whether said living body is exhaling or inhaling; and
   a parallel interface electrically connected between said respirator gating means and said computing means to provide said computing means with information concerning the operational status of said respirator gating means.

5. A method for analyzing physiological conditions within an organ of a living body comprising:
   transducing and converting values of pressure to an analog electrical signal waveform indicative of the variations of pressure over time within said organ of said body;
   converting said analog electrical signal waveform into digital electrical signals;
   measuring values of the pressure within said organ of said body over a period of time;
   mathematically analyzing the distribution of said digital electrical signals with Fourier transforms and centroid analysis of the frequency spectrum resulting from the transformation; and
   correlating the results of said mathematical analysis with physiological conditions within said organ of said body.

6. A method for analyzing physiological conditions within the brain of a living body comprising:

transducing and converting the measured values of intracranial pressure to an analog electrical signal waveform indicative of the variations of intracranial pressure over time within the brain of said body.

converting said analog electrical signal waveform into digital electrical signals;

measuring values of the intracranial pressure within the brain of said body over a period of time;

mathematically analyzing the distribution of said digital electrical signals with Fourier transforms and centroid analysis of the frequency spectrum resulting from the transformation; and correlating the results of said mathematical analysis with physiological conditions within the brain of said body.

7. A method for measuring the cerebral compliance of a brain within a living body comprising the steps of:

measuring values of the intracranial pressure within the brain of said body over a period of time;

converting the measured values of intracranial pressure to an analog electrical signal waveform indicative of the variations of intracranial pressure over time within the brain of said body;

converting said analog electrical signal waveform into digital electrical signals;

mathematically analyzing said digital electrical signals with Fourier transforms to obtain a frequency spectrum of the intracranial pressure waveform;

calculating the value of the centroid of a range of frequencies in said frequency spectrum around approximately eight (8.0) cycles per second; and correlating the calculated value of said centroid with known values of cerebral compliance to obtain a measurement of cerebral compliance.

8. A method for measuring the cerebral compliance of a brain within a living body on a continuous on-line real time basis comprising the steps of:

measuring values of the intracranial pressure within the brain of said body over a period of time;

converting the measured values of intracranial pressure to an anlog electrical signal waveform indicative of the variations of intracranial pressure over time within the brain of said body;

converting said analog electrical signal waveform into digital electrical signals;

mathematically analyzing said digital electrical signals with Fourier transforms to obtain a frequency spectrum of the intracranial pressure waveform;

calculating the value of the centroid of a range of frequencies in said frequency spectrum around approximately eight (8.0) cycles per second;

correlating the calculated value of said centroid with known values of cerebral compliance to obtain a measurement of cerebral compliance; and continuously repeating the above steps to obtain numerous on-line real time measurements of cerebral compliance over a period of time.

9. A method for measuring the cerebral blood flow of a brain within a living body comprising the steps of:

measuring values of the intracranial pressure within the brain of said body over a period of time;

converting the measured values of intracranial pressure to an analog electrical signal waveform indicative of the variations of intracranial pressure over time within the brain of said body;

converting said analog electrical signal waveform into digital electrical signals;

mathematically analyzing said digital electrical signals with Fourier transforms to obtain a frequency spectrum of the intracranial pressure waveform;

calculating the value of the centroid of a range of frequencies in said frequency spectrum around approximately one and one half (1.5) cycles per second; and correlating the calculated value of said centroid with known values of cerebral blood flow to obtain a measurement of cerebral blood flow.

10. A method for measuring the cerebral blood flow of a brain within a living body on a continuous on-line real time basis comprising the steps of:

measuring values of the intracranial pressure within the brain of said body over a period of time;

converting the measured values of intracranial pressure to an analog electrical signal waveform indicative of the variations of intracranial pressure over time within the brain of said body;

converting said analog electrical signal waveform into digital electrical signals;

mathematically analyzing said digital electrical signals with Fourier transforms to obtain a frequency spectrum of the intracranial pressure waveform;

calculating the value of the centroid of a range of frequencies in said frequency spectrum around approximately one and one half (1.5) Hz;

correlating the calculated value of said centroid with known values of cerebral blood flow to obtain a measurement of cerebral blood flow; and continuously repeating the above steps to obtain numerous on-line real time measurements of cerebral blood flow over a period of time.

11. A method for detecting when the cerebral blood flow in the brain of a living body is becoming dangerously low comprising the steps of:

measuring values of the intracranial pressure within the brain of said body over a period of time;

converting the measured values of intracranial pressure to an analog electrical signal waveform indicative of the variations of intracranial pressure over time within the brain of said body;

converting said analog electrical signal waveform into digital electrical signals;

mathematically analyzing said digital electrical signals with Fourier transforms to obtain a frequency spectrum of the intracranial pressure waveform;

calculating the value of the centroid of a range of frequencies in said frequency spectrum around approximately one and one half (1.5) Hz;

continuously repeating the above steps to obtain numerous on-line real time measurements of cerebral blood flow over a period of time; and correlating a decrease of cerebral blood flow over time with an increase in the mean intracranial pressure.

12. A method for detecting when the cerebral blood flow in the brain of a living body is becoming dangerously high comprising the steps of:

measuring values of the intracranial pressure within the brain of said body over a period of time;

converting the measured values of intracranial pressure to an analog electrical signal waveform indicative of the variations of intracranial pressure over time within the brain of said body;
converting said analog electrical signal waveform into digital electrical signals;
mathematically analyzing said digital electrical signals with Fourier transforms to obtain a frequency spectrum of the intracranial pressure waveform;
calculating the value of the centroid of a range of frequencies in said frequency spectrum around approximately one and one half (1.5) Hz;
continuously repeating the above steps to obtain numerous on-line real time measurements of cerebral blood flow over a period of time; and
correlating an increase in cerebral blood flow over time with significantly large increases and decreases in the mean intracranial pressure.

13. A method for detecting when the cerebral blood flow in the brain of a living body is uncontrolled comprising the steps of:
measuring values of the intracranial pressure within the brain of said body over a period of time;
converting the measured values of intracranial pressure to an analog electrical signal waveform indicative of the variations of intracranial pressure over time within the brain of said body;
converting said analog electrical signal waveform into digital electrical signals;
mathematically analyzing said digital electrical signals with Fourier transforms to obtain a frequency spectrum of the intracranial pressure waveform;
calculating the value of the centroid of a range of frequencies in said frequency spectrum around approximately one and one half (1.5) cycles per second;
continuously repeating the above steps to obtain numerous on-line real time measurements of cerebral blood flow over a period of time; and
correlating increases and decreases in the cerebral blood flow over time with decreases and increases in the mean intracranial pressure over time.

14. A method for detecting the development of a severe physiological problem in the brain of a living body comprising the steps of:
(a) measuring values of the intracranial pressure within the brain of said body over a period of time;
(b) converting the measured values of intracranial pressure to an analog electrical signal waveform indicative of the variations of intracranial pressure over time within the brain of said body;
(c) converting said analog electrical signal waveform into digital electrical signals;
(d) mathematically analyzing said digital electrical signals with Fourier transforms to obtain a frequency spectrum of the intracranial pressure waveform;
(e) calculating the value of the centroid of a range of frequencies in said frequency spectrum around approximately one and one half (1.5) Hz;
(f) continuously repeating steps (a) through (e) to obtain numerous on-line real time measurements of cerebral blood flow over a period of time;
(g) calculating the value of the centroid of a range of frequencies in said frequency spectrum around approximately eight (8.0) Hz;
(h) correlating the calculated value of said centroid with known values of cerebral compliance to obtain a measurement of cerebral compliance;
(i) continuously repeating the above steps to obtain numerous on-line real time measurements of cerebral compliance over a period of time; and
(j) correlating a sudden decrease in cerebral blood flow with a sudden increase in cerebral compliance.

15. An apparatus for analyzing changes in the waveform generated by variations of pressure within an organ of a living body, comprising:
pressure sensing means adapted to be placed within an organ of a living body for measuring the pressure within said organ of said body;
pressure transducer means connected to said pressure sensing means for converting the measured values of pressure to an analog electrical signal waveform indicative of the waveform generated by the variations of pressure over time within said organ of said body;
analog to digital converter means, electrically connected to said pressure transducer means, for converting said analog electrical signal waveform into digital electrical signals indicative of said pressure waveform, for digital computer analysis;
computing means electrically connected to said analog to digital converter means for mathematically computing, from said digital electrical signals, the value of a resonant frequency of said organ of said body, said resonant frequency indicative of a physiological condition in said organ of said body; and
output means electrically connected to said computing means for displaying the results of said computations.

16. An apparatus for analyzing changes in the waveform generated by variations of intracranial pressure within the brain of a living body comprising:
pressure sensing means adapted to be placed within the brain of a living body for measuring the intracranial pressure within the brain of said body;
pressure transducer means connected to said pressure sensing means for converting the measured values of intracranial pressure to an analog electrical signal indicative of the waveform generated by the variations of intracranial pressure over time within the brain of said body;
analog to digital converter means electrically connected to said pressure transducer means for converting said analog electrical signal waveform into digital electrical signals indicative of said intracranial pressure waveform, for digital computer analysis;
computing means electrically connected to said analog to digital converter means for mathematically computing, from said digital electrical signals, the value of a first resonant frequency of said brain of said body to indicate the cerebral compliance within said brain of said body; and
output means electrically connected to said computing means for displaying the results of said computations.

17. An apparatus as claimed in claim 16, wherein the computing means further is for computing, from said digital electrical signals, the value of a second resonant frequency of said brain of said body to indicate the cerebral blood flow within said brain of said body.

18. An apparatus as claimed in claim 17 together with electrocardiograph means adapted to be connected to said living body for measuring the analog electrical signals of the heart of said living body; and at least one signal line electrically connecting said electrocardiograph means and said analog to digital converter means, transmitting said analog electrical signals from said electrocardiograph means to said analog to digital converter means for conversion into digital electrical signals and subsequently to said computing means for correlation with the digital electrical signals indicative of the intracranial pressure waveform.

19. An apparatus as claimed in claim 18 together with respirator gating means connected within at least one signal line electrically connecting said electrocardiograph means and said analog to digital converter means for regulating the transmission of the electrical signal from said electrocardiograph means on said signal line to said analog to digital converter means;

a respirator pressure switch connected to a respirator adapted to be connected to said living body, said switch determining when said living body is breathing out and when said living body is breathing in, said respirator pressure switch electrically connected to said respirator gating means to provide said respirator gating means with information concerning whether said living body is breathing out or breathing in; and a parallel interface electrically connected between said respirator gating means and said computing means to provide said computing means with information concerning the operational status of said respirator gating means.

20. An apparatus as claimed in claim 16 together with electrocardiograph means adapted to be connected to said living body for measuring the analog electrical signals of the heart of said living body; and at least one signal line electrically connecting said electrocardiograph means and said analog to digital converter means, transmitting said analog electrical signals from said electrocardiograph means to said analog to digital converter means for conversion into digital electrical signals and subsequently to said computing means for correlation with the digital electrical signals indicative of the intracranial pressure waveform.

21. An apparatus as claimed in claim 20 together with respirator gating means connected within at least one signal line electrically connecting said electrocardiograph means and said analog to digital converter means for regulating the transmission of the electrical signal from said electrocardiograph means on said signal line to aid analog to digital converter means;

a respirator pressure switch connected to a respirator adapted to be connected to said living body, said switch determining when said living body is exhaling and when said living body is inhaling, said respirator pressure switch electrically connected to said respirator gating means to provide said respirator gating means with information concerning whether said living body is exhaling or inhaling; and a parallel interface electrically connected between said respirator gating means and said computing means to provide said computing means with information concerning the operational status of aid respirator gating means.

22. A method for analyzing physiological conditions within an organ of a living body comprising:

measuring values of the pressure within said organ of said body over a period of time;

converting the measured values of pressure to an analog electrical signal waveform indicative of a waveform generated by the variations of pressure over time within said organ of said body;

converting said analog electrical signal waveform into digital electrical signals indicative to said pressure waveform;

mathematically computing, from said digital electrical signals, a resonant frequency of said organ of said body; and correlating said resonant frequency with a physiological condition within said organ of said body.

23. A method for analyzing physiological conditions within the brain of a living body comprising:

measuring values of the intracranial pressure within the brain of said body over a period of time;

converting the measured values of intracranial pressure to an analog electrical signal waveform indicative of the waveform generated by the variations of intracranial pressure over time within said body, converting said analog electrical signal waveform into digital electrical signals indicative of said intracranial pressure waveform;

mathematically computing, from said digital electrical signals, a resonant frequency of the brain of said body; and correlating said resonant frequency with a physiological condition within the brain of said body.

* * * * *